US012629149B2

(12) United States Patent (10) Patent No.: US 12,629,149 B2
Estevez et al. (45) Date of Patent: May 19, 2026

(54) LOCKING MECHANISMS FOR GRASPING DEVICES AND METHODS OF USE

(71) Applicant: Boston Scientific Scimed, Inc, Maple Grove, MN (US)

(72) Inventors: Ramon Estevez, Lowell, MA (US); Paul Smith, Smithfield, RI (US); Kathryn Venuto, Waltman, MA (US); Christopher R. Deuel, Melrose, MA (US); Douglas Melanson, Natick, MA (US); Ian Bourdon, Southborough, MA (US)

(73) Assignee: Boston Scientific Scimed, Inc, Maple Grove, MN (US)

( * ) Notice: Subject to any disclaimer, the term of this patent is extended or adjusted under 35 U.S.C. 154(b) by 0 days.

(21) Appl. No.: 18/530,461

(22) Filed: Dec. 6, 2023

(65) Prior Publication Data

US 2024/0099717 A1 Mar. 28, 2024

Related U.S. Application Data

(63) Continuation of application No. 17/165,452, filed on Feb. 2, 2021, now Pat. No. 11,883,023.

(60) Provisional application No. 62/969,725, filed on Feb. 4, 2020.

(51) Int. Cl.
*A61B 17/068* (2006.01)
*A61B 17/072* (2006.01)

(52) U.S. Cl.
CPC ........ *A61B 17/0686* (2013.01); *A61B 17/072* (2013.01); *A61B 2017/07257* (2013.01); *A61B 2017/07285* (2013.01)

(58) Field of Classification Search
CPC ............ A61B 17/0684; A61B 17/0686; A61B 17/072; A61B 17/07278; A61B 17/07264; A61B 2017/07257; A61B 2017/07285; A61B 2017/0725; A61B 17/2833; A61B 2017/2946
USPC ............................. 227/175.1–182.1; 606/139
See application file for complete search history.

(56) References Cited

U.S. PATENT DOCUMENTS

| | | | |
|---|---|---|---|
| 4,580,712 A | 4/1986 | Green | |
| 5,474,223 A | 12/1995 | Viola et al. | |
| 5,507,773 A * | 4/1996 | Huitema | A61B 17/29 606/174 |
| 5,626,607 A | 5/1997 | Malecki | |
| 5,993,464 A * | 11/1999 | Knodel | A61B 17/115 606/139 |
| 7,059,331 B2 | 6/2006 | Adams et al. | |
| 8,328,061 B2 | 12/2012 | Kasvikis | |

(Continued)

FOREIGN PATENT DOCUMENTS

| | | |
|---|---|---|
| CA | 3075058 | 9/2020 |
| CN | 103124529 A | 5/2013 |

(Continued)

*Primary Examiner* — Shelley M Self
*Assistant Examiner* — Linda J. Hodge
(74) *Attorney, Agent, or Firm* — Bookoff McAndrews PLLC

(57) ABSTRACT

A tissue fastening device includes a body including a plurality of sidewalls defining a channel, an anvil having a proximal end and a distal end and pivotally coupled to the body and the anvil moves between an open position and a closed position, and a locking mechanism to lock the anvil in the closed position.

14 Claims, 18 Drawing Sheets

(56) References Cited

U.S. PATENT DOCUMENTS

| | | | |
|---|---|---|---|
| 10,278,699 B2 | 5/2019 | Thompson et al. | |
| 11,259,808 B2 | 3/2022 | George et al. | |
| 2007/0010838 A1 | 1/2007 | Shelton et al. | |
| 2007/0084899 A1 | 4/2007 | Taylor | |
| 2007/0175961 A1 | 8/2007 | Shelton et al. | |
| 2007/0175964 A1 | 8/2007 | Shelton et al. | |
| 2007/0215670 A1 | 9/2007 | Hoffman | |
| 2008/0017693 A1 | 1/2008 | Mastri et al. | |
| 2011/0186614 A1* | 8/2011 | Kasvikis | A61B 17/07207 |
| | | | 227/176.1 |
| 2012/0181322 A1* | 7/2012 | Whitman | A61B 17/068 |
| | | | 227/176.1 |
| 2014/0188138 A1 | 7/2014 | Melsheimer et al. | |
| 2015/0173756 A1 | 6/2015 | Baxter, III et al. | |
| 2015/0190191 A1* | 7/2015 | Strobl | A61B 18/1445 |
| | | | 606/167 |
| 2016/0058439 A1* | 3/2016 | Shelton, IV | A61B 17/105 |
| | | | 227/176.1 |
| 2016/0287253 A1 | 10/2016 | Shelton, IV | |
| 2018/0168639 A1 | 6/2018 | Shelton, IV et al. | |
| 2018/0168642 A1 | 6/2018 | Shelton, IV | |
| 2018/0289371 A1 | 10/2018 | Wang et al. | |
| 2018/0353179 A1 | 12/2018 | Shelton, IV et al. | |
| 2019/0059984 A1 | 2/2019 | Otrembiak et al. | |
| 2019/0298346 A1 | 10/2019 | Shelton, IV et al. | |
| 2019/0321062 A1 | 10/2019 | Williams | |
| 2021/0145440 A1* | 5/2021 | Thompson | A61B 17/07207 |
| 2021/0161526 A1 | 6/2021 | Srinivas et al. | |

FOREIGN PATENT DOCUMENTS

| | | | | |
|---|---|---|---|---|
| CN | 106963434 A | | 7/2017 | |
| CN | 108024808 A | | 5/2018 | |
| DE | 102009055747 A1 | * | 6/2011 | A61B 17/062 |
| EP | 2316366 A2 | | 5/2011 | |
| EP | 2992835 A2 | | 3/2016 | |
| EP | 3578115 A1 | | 12/2019 | |
| JP | H08509404 A | | 10/1996 | |
| JP | H09262243 A | | 10/1997 | |
| JP | 2010-504807 A | | 2/2010 | |
| JP | 2013-541999 A | | 11/2013 | |
| WO | 2018/152044 A1 | | 8/2018 | |

* cited by examiner

LOCKING MECHANISMS FOR GRASPING DEVICES AND METHODS OF USE

CROSS-REFERENCE TO RELATED APPLICATIONS

This application is a continuation of U.S. application Ser. No. 17/165,452, filed Feb. 2, 2021, which claims the benefit of priority from U.S. Provisional Application No. 62/969, 725, filed on Feb. 4, 2020, each of which which is incorporated by reference herein in its entirety.

TECHNICAL FIELD

The present disclosure relates generally to minimally invasive (e.g., endoscopic and/or laparoscopic) medical devices and related methods of use. More particularly, in some embodiments, the disclosure relates to one or more locking mechanisms for tissue fastening devices, e.g., stapler devices, and related methods of use, among other aspects.

BACKGROUND

Technological developments have given users of medical systems, devices, and methods, the ability to conduct increasingly complex procedures on subjects. The coupling of tissue in, for example, a subject's gastrointestinal tract or other locations within the body, is a type of procedure in which difficulties may arise. Surgical devices that grasp or clamp tissue between opposing jaw structures and then join the tissue by surgical fasteners are known. The fasteners may include surgical staples. In some procedures, a cutting instrument may be provided to cut the tissue which has been joined by the fasteners. Drawbacks of these systems include, for example, maintaining jaws of a tissue fastener in a closed configuration to provide sufficient compression of tissue during cutting and/or stapling of tissue, and/or additional medical procedures. For example, proximal movement alone of a flexible pulling mechanism, e.g., a wire, may not provide sufficient compression of tissue during stapling. Thus, tissue may not be properly stapled and/or cut, which may increase therapy time and/or cost, may cause undesired or incomplete fastening of tissues, and/or may require additional therapy/intervention at the target site. The present disclosure may solve one or more of these problems or other problems in the art. The scope of the disclosure, however, is defined by the attached claims and not the ability to solve a specific problem.

SUMMARY OF THE DISCLOSURE

According to an aspect, a tissue fastening device comprises a body including a plurality of sidewalls defining a channel, an anvil having a proximal end and a distal end and pivotally coupled to the body, wherein the anvil is configured to move between an open position and a closed position, and a locking mechanism configured to lock the anvil in the closed position.

The locking mechanism may include (1) a ramp having a sloped surface angled toward a proximal end of the body and (2) a top surface parallel to a bottom surface of the body.

The proximal end of the anvil may be configured to engage and slide along the ramp as the anvil is moved in a proximal direction.

The anvil may be locked in the closed position when the proximal end of the anvil is disposed on the top surface of the ramp.

The anvil may include an anvil notch extending into a surface of the anvil, and the anvil notch may be configured to engage the locking mechanism to lock the anvil in the closed position.

The locking mechanism may include a clip on the body and the clip may be configured to engage the anvil notch.

The clip may include a clip protrusion extending from a top surface of the clip, and the clip protrusion may be configured to engage the anvil notch when the anvil is in the closed position.

The tissue fastening device may further include a clip wire connected to a bottom surface of the clip and extending proximal to the clip, wherein a proximal movement of the clip wire may be configured to move the clip away from the anvil and to disengage the clip protrusion from the anvil notch.

The locking mechanism may include a pin wire extending in a proximal direction and having a locking pin attached to a distal end of the locking wire, and wherein the locking pin may engage the anvil notch in the closed position.

The anvil notch may face a proximal direction when the anvil is in the locked position.

The tissue fastening device may further comprise a pulley, wherein the pin wire may be configured to engage the pulley.

The tissue fastening device may further comprise a biasing mechanism extending within the body and connected to the locking pin, and wherein the biasing member may be configured to bias the locking pin toward the anvil.

The body may include a slot in opposing sidewalls of the body, wherein the anvil may include a pin extending from opposing sidewalls, and wherein each pin may be configured to engage a corresponding slot in the body and may slide relative to the body within the slot.

The anvil may be substantially parallel to the body when the anvil is locked in the closed position by the locking mechanism.

The body may include a slot in one of the plurality of sidewalls of the body and extending along a longitudinal axis, and a distally facing recess disposed on the longitudinal axis and distal to the slot, wherein a plurality of pins may extend from the anvil, wherein a first pin from the plurality of pins may engage the slot, and wherein a second pin from the plurality of pins may be configured to engage the recess to lock the anvil in the closed position.

According to another aspect, a tissue fastening device comprises a body including a plurality of sidewalls defining a channel, wherein one sidewall of the plurality of sidewalls includes a slot extending along a longitudinal axis, an anvil having a proximal end, a distal end, and a pin pivotally coupling the anvil to the body via the slot, wherein the anvil is configured to move between an open position and a closed position, a first protrusion extending from a top wall of the slot toward the longitudinal axis, and a second protrusion extending from a bottom wall of the slot toward the longitudinal axis, wherein the protrusions are configured to engage the pin and lock the anvil in the closed position.

The first and second protrusions may include ball-nose spring plungers, and wherein the pin may be configured to push the first and second protrusions away from the longitudinal axis as the pin moves proximal or distal to the first and second protrusions.

According to another aspect, a method of fastening tissue comprises advancing a tissue fastening device including an anvil pivotally connected to a body to a target site within a patient, moving a wire connected to the anvil in a proximal direction to cause the anvil to rotate from an open position to a closed position, and advancing a locking pin into an anvil notch extending into the anvil to lock the anvil in the closed position.

The method may further include performing one or more of a stapling or a cutting of the tissue after the anvil is in the closed position, and withdrawing, after performing the one or more of the stapling or the cutting, the locking pin from the anvil slot.

The withdrawing may include overcoming a biasing force of a biasing member connected to the locking pin.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1:
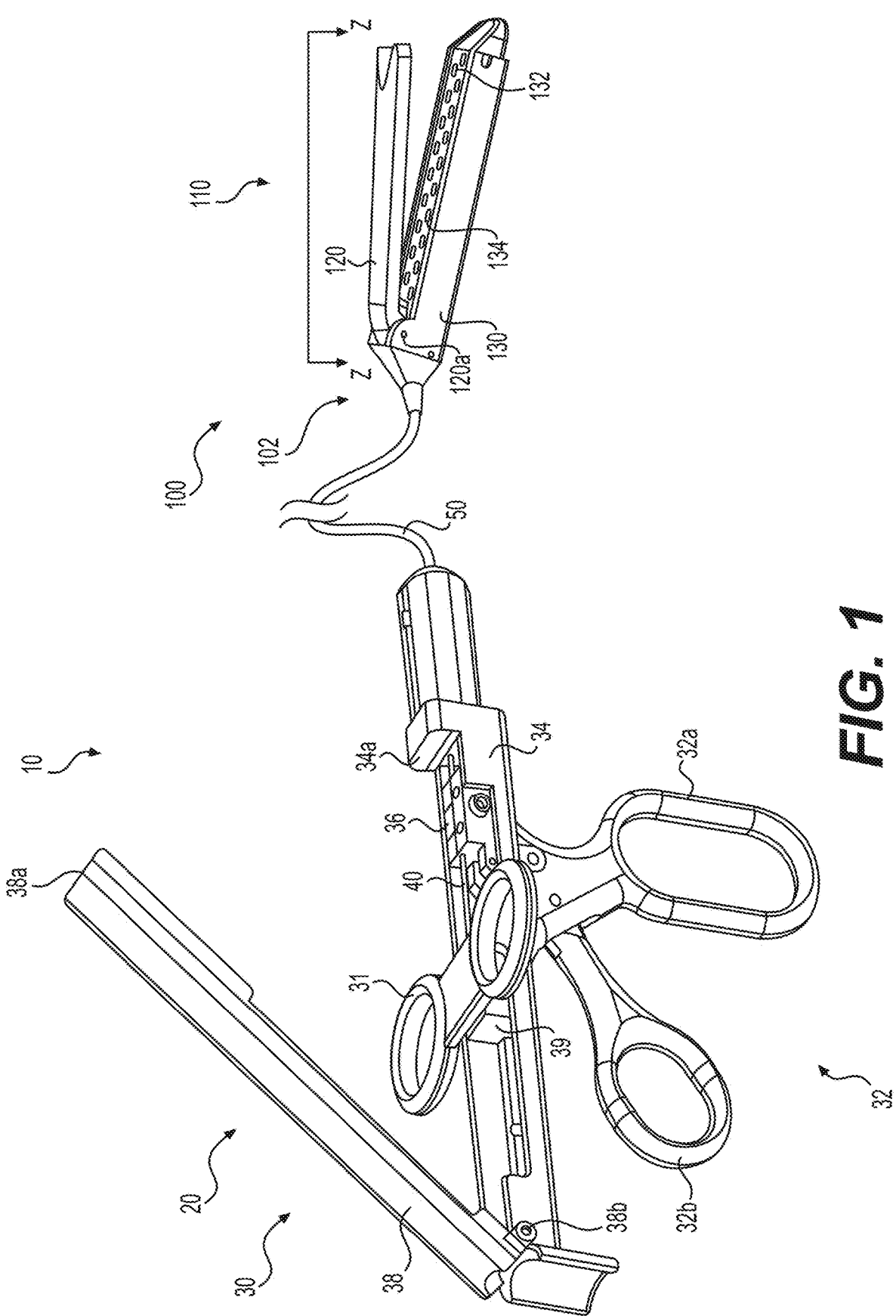
FIG. 1 is a schematic view of a tissue fastening system according to an embodiment.

The present disclosure is described with reference to exemplary medical systems and medical tools for accessing a target site, for example, for grasping, cutting, and/or stapling tissue. This may provide improved medical tool functionality and/or may assist medical professionals to improve cutting and/or fastening of tissue. In some examples, ensuring a proper alignment between an anvil and a body of a stapler may provide improved stapling of tissue. However, it should be noted that reference to any particular device and/or any particular procedure is provided only for convenience and not intended to limit the disclosure. A person of ordinary skill in the art would recognize that the concepts underlying the disclosed devices and application methods may be utilized in any suitable procedure, medical or otherwise. The present disclosure may be understood with reference to the following description and the appended drawings, wherein like elements are referred to with the same reference numerals.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, "extends distally" indicates that a component extends in a distal direction, and "extends proximally" indicates that a component extends in a proximal direction. Further, as used herein, the terms "about," "approximately" and "substantially" indicate a range of values within +/−10% of a stated or implied value. Additionally, terms that indicate the geometric shape of a component/surface refer to exact and approximate shapes.

Embodiments of the present disclosure may be used to cut and/or fasten tissue in an endo-luminal space, or facilitate the process thereof. According to an example, the fastening device may be a tissue stapling apparatus, which may include a resection or cutting mechanism (e.g., an integrated knife) and a stapling mechanism (e.g., a stapler). The stapling device may be delivered through an endoscope working channel to the target tissue site. All or parts of the tissue stapling device and the retraction mechanism could be metallic, plastic, or include a shape memory metal (such as nitinol), a shape memory polymer, a polymer, or any combination of materials. While reference is made herein to a stapling device, the described locking may be used with any device having an opposing jaw design for grasping tissue therebetween.

FIG. 1 shows a surgical apparatus 10 in accordance with an example of this disclosure. Apparatus 10 may be a surgical stapling apparatus configured to engage body tissue, and apply a plurality of surgical fasteners thereto during minimally invasive surgical procedures, such as laparoscopic or endoscopic procedures. In some embodiments apparatus 10 may be a suturing apparatus to delivering a suture for tissue closure during minimally invasive surgical procedures. Apparatus 10 may be used to apply a suture, surgical clips, or other fasteners, but will be primarily discussed in the context of grasping tissue in preparation of performing additional procedures to the tissue, e.g., stapling and/or cutting the tissue.

As illustrated in FIG. 1, apparatus 10 includes a proximal section 20 and a distal section, e.g., an end effector 100. Surgical apparatus 10 also includes a handle assembly 30, an elongated body 50, and a stapler device 110 at end effector 100. Elongated body 50 may extend any length suitable for endoscopic or laparoscopic procedures, and may be configured to be positioned within a working channel of an endoscope. Elongated body 50 may be detachable from handle assembly 30 to facilitate insertion of elongated body 50 into a working channel of an endoscope or a channel of another device, for example by backloading elongated body 50 into the working channel. In some examples, elongated body 50 may be flexible, steerable, and/or may be rotatable about its axis. Elongated body 50 may include a lumen for positioning actuation wires within for actuating stapler device 110 via handle assembly 30 or actuating any other portion of apparatus 10. Elongated body 50 may be configured to receive a plurality of actuation wires or a single actuation wire (for example, actuation wire 40). In some examples, elongated body 50 may be fixedly coupled to stapler device 110, and in other examples elongated body 50 may be removably or releasably coupled to stapler device 110. Unless stated otherwise, any wire or actuation device described herein may extend from handle assembly 30 to end effector 100 via a lumen of elongated body 50.

Handle assembly 30 may include a handle 32 and a body 34. Handle 32 may include a fixed portion 32a and an actuator portion 32b. Fixed portion 32a of handle 32 may be fixedly coupled to body 34. Actuator portion 32b may include a circular or oval portion or ring for positioning a user's fingers within, which may assist a user in holding handle assembly 30. In some examples, actuator portion 32b of handle 32 may be an actuator which may be pivotally coupled to body 34 and movable relative to fixed portion 32a of handle 32. In some examples, actuator portion 32b of handle 32 may be coupled to a proximal portion of an actuation wire, such as actuation wire 40, via an adjustable coupler 36. An anvil (e.g., anvil 120) of stapler device 110 may be actuated via actuation wire 40 extending between stapler device 110 and handle assembly 30. In other examples, actuator portion 32b of handle 32 may be configured to control any other mechanism of apparatus 100, such as actuation of the deployment of staples from stapler device 110. It will be understood that wire 40 has sufficient rigidity to be pushed in the distal direction and pulled in the proximal direction.

In some examples, handle assembly 30 may include a moveable cover 38 pivotally coupled to housing 34 at pivot point 38b. In FIG. 1, cover 38 is shown in an open position, exposing the internal portions of body 34. Cover 38 may be coupled to a proximal portion of body 34 and may cover the internal components of handle assembly 30 when positioned in a closed configuration, e.g., when a distalmost end 38a of cover 38 faces a surface 34a of body 34. Cover 38 may be temporarily fixedly coupled to a position covering the internal components of body 34 via a coupling mechanism at a distal portion of cover 38 and a distal portion of handle assembly 30, such as a snap-fit mechanism or the like. When in the closed configuration, cover 38 may form a pair of slots in body 34 (not shown). When the distal portion of cover 38 is uncoupled from the distal portion of body 34, a user may rotate (or pivot) cover 38 at pivot point 38b in order to have access to the internal components of handle assembly 30.

Handle assembly 30 may include one or more adjustable couplers 36, 39, which may be configured to receive a portion of an actuation wire, such as actuation wire 40. Any of adjustable couplers 36, 39 may be a vice which is moveable in order to clamp down onto actuation wire 40 and fixedly couple actuation wire to the adjustable couplers 36, 39. In some examples, adjustable couplers 36, 39 may be moveable via a screw to adjust couplers 36, 39 and couple or uncouple actuation wire 40 from couplers 36, 39. Couplers 36, 39 may be used in the movement of additional wires described herein.

Adjustable coupler 39 may be coupled to longitudinal actuator 31 and moveable longitudinally via translating longitudinal actuator 31 within body 34. Longitudinal actuator 31 may be partially positioned within housing 34 and may be slidable longitudinally within the two slots formed when cover 38 is positioned over the internal components of handle assembly 30. Longitudinal actuator 31 may include a pair of opposing circular or oval portions or rings, with each circular portion defining an aperture for a user to position their fingers within. In some examples, longitudinal actuator 31 may be coupled to an actuation wire (not shown), such as via adjustable coupler 39 or via a different coupler within body 34, and may be configured to control staple deployment from stapler device 110. In other examples, longitudinal actuator 31 may be configured to control any other mechanism of apparatus 10, such as actuation of anvil 120 of stapler device 110.

End effector 100 of apparatus 10 includes a stapler device 110 coupled to a distal portion of elongated body 50. A connector 102 of stapler device 110 may couple elongated body 50 to stapler device 110. In some examples, connector 102 may be offset from a longitudinal axis of a body 130 of stapler device 110. Body 130 of stapler device 110 may include a cartridge 132 positioned within a channel of body 130. Cartridge 132 may be fixedly coupled to body 130 or may be removable from body 130. In some examples, cartridge 132 may be integrally formed in body 130. At a proximal portion of body 130, an anvil 120 may be rotatably or pivotally coupled to body 130 via pin 120a (pin 120a may define a pivot axis), and may extend distally towards a distal end of stapler device 110. In some examples, anvil 120 may be rotatably biased and may be biased to an open configuration, e.g., biased away from body 130 and cartridge 132 using a spring or the like, thereby creating a space between a distal portion of anvil 120 and a distal portion of body 130 and cartridge 132. Anvil 120 may be rotatable about pin 120a to contact body 130, or retain tissue between anvil 120 and body 130, and provide a surface for which staples may be driven against when ejected from cartridge 132. For ease of understanding, pin 120a and corresponding openings or slots will be described herein in the singular, i.e., with reference to only a single side of the stapler device. Unless stated otherwise, an opposite side of the stapler device will have the same elements oriented in the same manner as described in each example (e.g., the opposite side of the stapler device may be a mirror image of the disclosed elements). For example, if a pin extends from an anvil and the pin moves within a slot on a first side of the stapler device, a second pin is positioned on an opposite side of the anvil and slides within a similarly positioned slot on the opposite side of the stapler device.

In some examples, body 130 may include a channel that supports cartridge 132. Cartridge 132 may contain a plurality of surgical fasteners, such as staples, and the fasteners may be deployed from cartridge 132 when under the influence of a driving force exerted by an actuation sled. A plurality of spaced apart longitudinal slots 134 in cartridge 132 allow staples to pass through cartridge 132 and pierce tissue. In some examples, an actuation sled moves proximally in the longitudinal direction from a distal end of cartridge 132 and/or body 130 when actuated, contacting fasteners within cartridge 132 and pushing fasteners through longitudinal slots 134 in order to couple fasteners to tissue. In some examples, a single fastener may extend through each slot 134. Each fastener may be partially within slot 134 prior to deployment to assist with alignment of the fastener with slot 134. In some examples, multiple actuation sleds may actuate two different longitudinal rows of fasteners in cartridge 132. To assist in providing a proper fastening of tissue, a locking mechanism may be provided on stapler device 110. For ease of understanding, reference will be made to cartridge 132 generally, and slots 134 will not be shown. It will be understood that each locking mechanism described herein may maintain a substantially parallel arrangement between anvil 120 and body 130 during stapling, suturing, or the like, which may improve connection between the tissue.

Figure 2A:
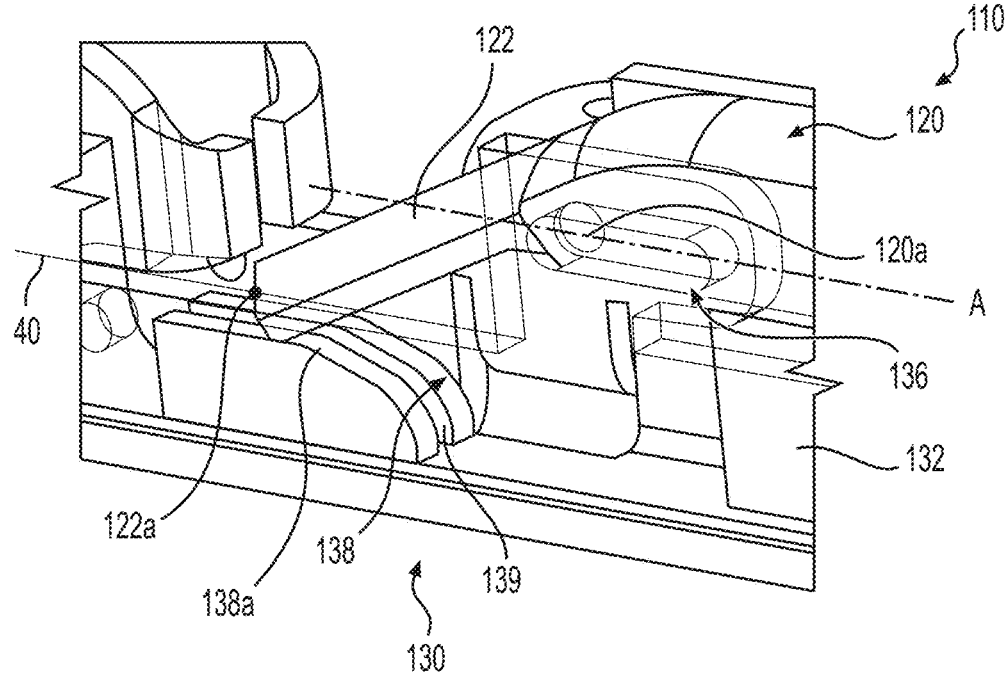
FIGS. 2A and 2B are views of a fastening device of the fastening system of FIG. 1, according to an embodiment.
Figures 3A, 3B, 3C:
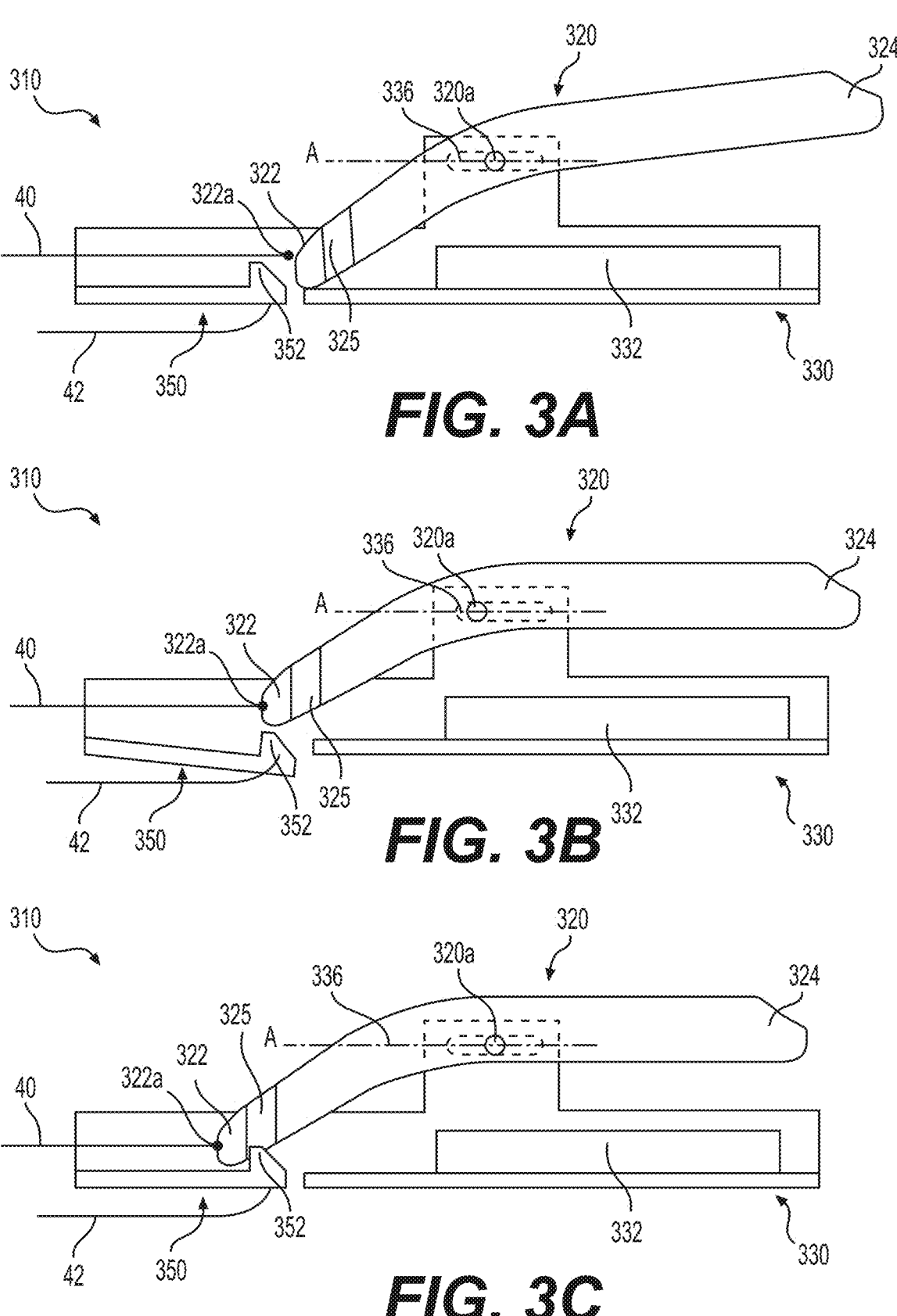
FIGS. 3A-3C are cross-section views along the line Z-Z of a fastening device of the fastening system of FIG. 1, according to an embodiment.

FIG. 2A shows an example of a locking mechanism for maintaining a position of anvil 120 during a fastening procedure. Anvil 120 may include a pin 120a extending from a side thereof. Pin 120a extends from a side wall of anvil 120 and may be disposed in a slot 136 on a side of body 130. Pin 120a of anvil 120 may move within a respective slot 136, which has a generally oval shape and extends in a longitudinal direction along a longitudinal axis A. Anvil 120 may also rotate about pins 120a. For example, when pin 120a is located at a distal end of slot 136, anvil 120 may be positioned in the open configuration, as shown in FIG. 3B, and anvil 120 may be in the closed position when pins 120a are positioned at a proximal end of slot 136. Wire 40 may be attached at a proximal end 122 of anvil 120 via an attachment mechanism 122a. Proximal movement of wire 40 may cause anvil 120 to move proximally and/or may cause anvil 120 to rotate about pin 120a. A diameter of pin 120a is approximately ⅙₆". A length of slot 136 is approximately ¼", and a height of slot 136 is approximately ⅙₆", but is sized to allow pin 120a to slide therein (e.g., the height of slot 136 is approximately equal to, but greater than, the diameter of pin 120a). Slot 136 may be disposed in an upper extension of body 130. In some embodiments, the upper extension may extend up and to the right, i.e., toward the distal end of body 130. In other embodiments, the upper extension of body 130 may only extend up. In yet other embodiments, a space may be disposed between the upper extension and the body 130. It will be understood that the upper extension may be used with any stapler body described in the examples herein.

Body 130 of stapler device 110 may include a ramp 138 having a rounded or curved distal end, such that the proximal end of ramp 138 is higher than the distal end of ramp 138. Ramp 138 may include two parallel ramps that form a channel 139 therebetween, as shown in FIG. 2A. Alternatively, a single ramp 138 may be provided and attachment mechanism 122a may be offset to allow wire 40 to move without being impeded by ramp 138. Wire 40 may move proximally and/or distally within slot 139 to move anvil 120 proximally and/or distally. For example, as anvil 120 is moved proximally, proximal end 122 may contact the curved distal end of ramp 138, causing proximal end 122 to move up ramp 138. As anvil 120 is moved proximally, pin 120a moves proximally within slot 136 along longitudinal axis A. At a same time, anvil 120 rotates about pin 120a, forcing a distal end 124 of anvil 120 toward cartridge 132. When pin 120a is at the distal end of slot 136, anvil 120 has rotated completely toward cartridge 132 into the closed configuration. Contact between proximal end 122 and ramp 138 provides a sufficient friction force to maintain the closed configuration of anvil 120. This may allow, for example, tissue to be grasped between anvil 120 and body 130 to perform additional medical procedures.

Figure 2B:
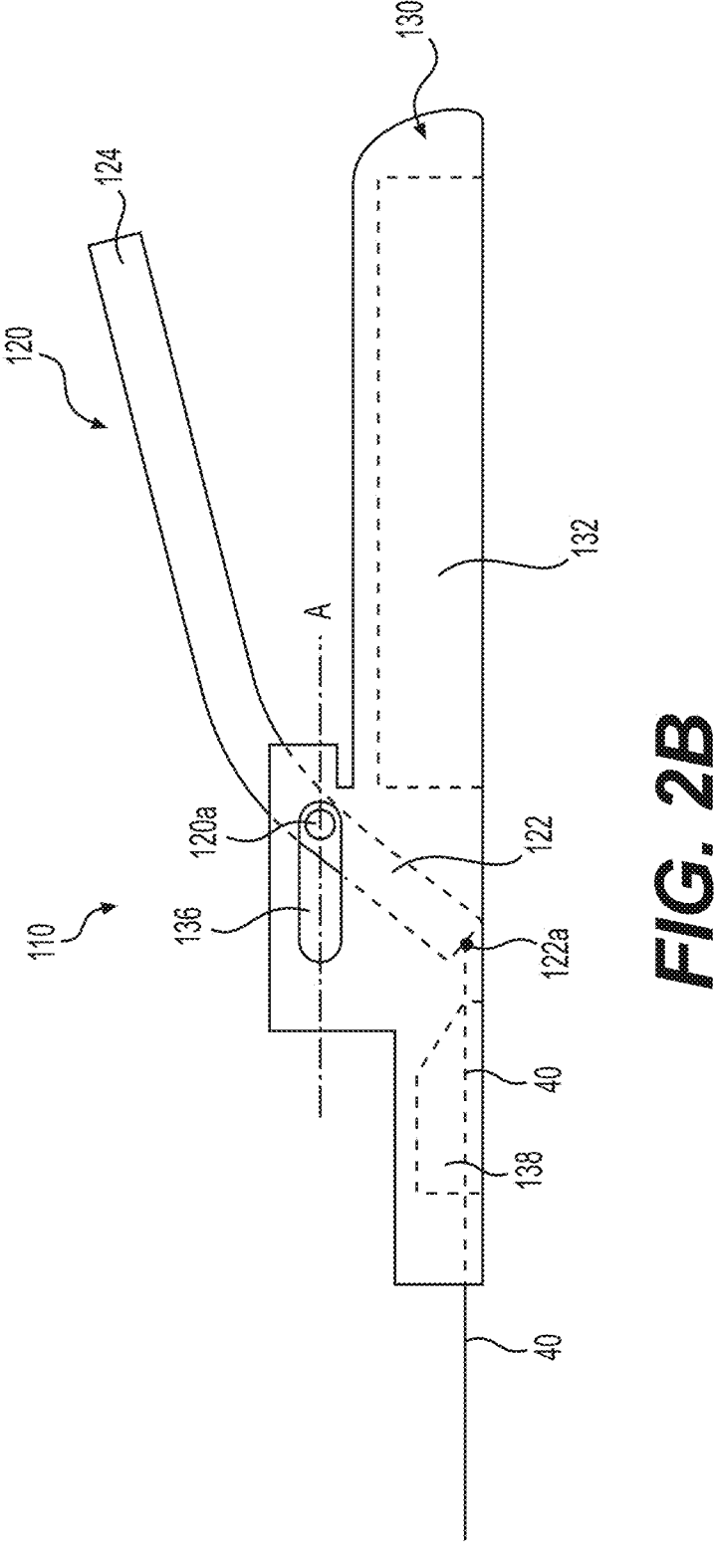

A method of operating anvil 120 will now be explained. Anvil 120 may be in an open configuration when pin 120a is at a distal end of slot 136, as shown in FIG. 2B. In the open configuration, tissue may be inserted between anvil 120 and body 130 of stapler device 110. A user may subsequently move wire 40 in a proximal direction, causing proximal end 122 to move proximally and contact ramp 138. Continued proximal movement of wire 40 causes proximal end 122 to travel up the curved/sloped surface 138a of ramp 138. This proximal movement also causes pin 120a to move proximally within slot 136 along longitudinal axis A. Movement of proximal end 122 up sloped surface 138a of ramp 138 causes anvil 120 to rotate about pin 120a. Pivoting anvil 120 about pin 120a causes distal end 124 of anvil 120 to move toward cartridge 132, grasping tissue and/or any other material between anvil 120 and cartridge 132. In this manner, anvil 122 may be locked against tissue during the fastening procedure to assist in providing accurate fastening.

Subsequently, additional medical procedures may be performed on the tissue or material grasped between anvil 120 and cartridge 132, e.g., the tissue may be fastened together via one or more staples. As another example, the tissue may be cut or other medical procedures may be performed on the grasped tissue. Once the additional medical procedures are complete, wire 40 may be moved distally, thereby moving proximal end 122 of anvil 120 down ramp 138. As proximal end 122 moves down ramp 138, pin 120a slides distally within slot 136 along longitudinal axis A, and anvil 120 pivots about pin 120a such that distal end 124 rotates away from cartridge 132.

Another example of a locking mechanism for a stapler device 310 is shown in FIGS. 3A-3C. A body 330 of stapler device 310 includes a slot 336 having a longitudinal axis A. A pin 320a extends from an anvil 320 into slot 336. Pin 320a is configured to slide within slot 336 along longitudinal axis A, and anvil 320 is configured to rotate about pin 320a. Anvil 320 includes a distal end 324 and a proximal end 322, with proximal end 324 being attached to wire 40 via an attachment mechanism 322a. A slot 325 extends into anvil 320 from a bottom surface of proximal end 322, and may extend through anvil 320 to a top surface of proximal end 322. As with other stapler devices, a cartridge 332 is disposed in body 330.

A clip 350 having a protrusion 352 extending vertically from a distal end of clip 350 is shown in FIG. 3A. Clip 350 may form part of body 330 from a distal end of elongated member 50, or clip 350 may extend from a proximal end of surgical apparatus 10 and along a catheter or other lumen, e.g., a lumen of elongated body 50. Protrusion 352 is configured to be inserted into slot 325 and lock anvil 320 in the closed configuration, as will be described herein. An actuation wire 42 is attached to the distal end of clip 350 on a bottom side thereof, i.e., a side opposite protrusion 352. Actuation wire 42 is configured to be moved in a proximal direction and a distal direction. Clip 350 may be biased in the position shown in FIGS. 3A and 3C by, e.g., a spring or other biasing element. Movement of actuation wire 42 in a proximal direction causes clip 350, including protrusion 352, to bend downwards and away from anvil 320 based on the material, e.g., a plastic, of clip 350. It will be understood, however, that the distal end of clip 350 including protrusion 352 may be hinged, such that movement of actuation wire 42 in proximal direction causes the distal end of clip 350 to rotate downwards and movement of actuation wire 42 in the distal direction causes the distal end of clip 350 to rotate upwards into the position shown in FIGS. 3A and 3C.

A method of operating stapler device 310 will now be described. Stapler device 310 may be advanced to a target site in any manner described herein. Wire 40 may move proximally, causing pin 320a (and anvil 320) to move proximally along longitudinal axis A and causing anvil to pivot about pin 320a. Moving wire 40 in a proximal direction may cause wire 40 to move upwards, e.g., toward pin 320a, causing proximal end 322 to move upwards and rotate anvil 320. Anvil 320 may also be rotated by sliding proximal end 322 up the sloped portion of protrusion 352 of clip 350. Additionally, or alternatively, when pin 320a is a proximal end of slot 336, anvil 320 may rotate about pin 320a. The proximal movement and rotation of anvil 320 may cause proximal end 322 to move proximally such that protrusion 352 of clip 350 engages slot 325, as shown in FIGS. 3B and 3C. This rotation causes distal end 324 to be moved toward body 330 and the closed configuration. Once protrusion 352 engages slot 325, anvil 320 may be locked in a stationary position, e.g., in the closed configuration. To unlock anvil 320, a user may move actuation wire 42 proximally, causing clip 350 to move downward, thereby disengaging protrusion 352 from slot 325. At a same time, the user may push wire 40 in a distal direction, which causes pin 320a to move distally along longitudinal axis A, thereby moving slot 325 distal of protrusion 352 to unlock anvil 320. Unlocking anvil 320 allows anvil 320 to move freely to the open configuration.

Figure 4A:
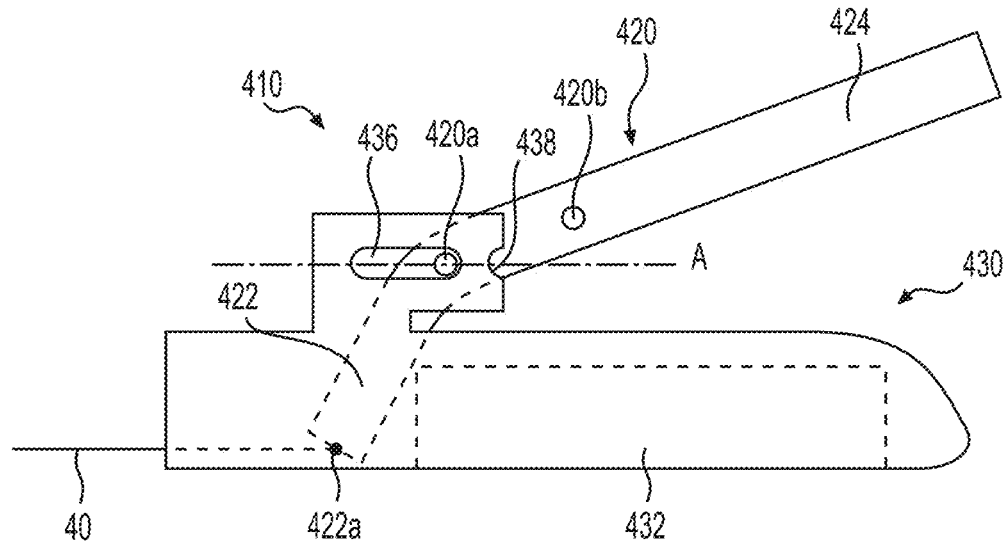
FIGS. 4A and 4B are views of a fastening device of the fastening system of FIG. 1, according to an embodiment.
Figure 4B:
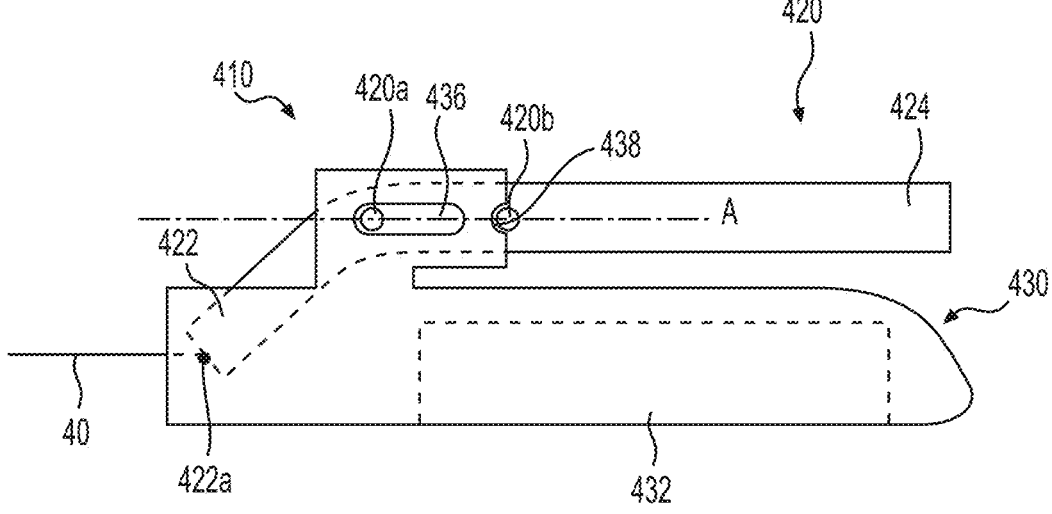

FIGS. 4A and 4B illustrate another locking mechanism according to another example of the present disclosure. An anvil 420 includes a first pin 420a and a second pin 420b extending from a same sidewall of anvil 420. Wire 40 is attached to a proximal end 422 of anvil 420 by an attachment mechanism 422a. Anvil 420 may pivot about first pin 420a, and pin 420a may move proximally and distally within a slot 436 in body 430 and along a longitudinal axis A. A recess 438 is formed in body 430 distally of slot 436 and along longitudinal axis A. In the open configuration, second pin 420b may be disengaged from recess 438. In the closed configuration, second pin 420b may slide into and engage recess 438, thereby locking anvil 420 in the closed configuration.

Stapler device 410 operates similarly to other example stapler devices described herein. Proximal movement of wire 40 causes pin 420a to slide proximally along longitudinal axis A within slot 436, moving anvil 420 proximally. The proximal movement of wire 40 also cases anvil 420 to rotate about pin 420a. The proximal movement of anvil 420 and the rotation of anvil 420 about pin 420a causes distal end 424 to rotate toward and approach body 430, causing second pin 420b to lie approximately along longitudinal axis A and to align with recess 438. Pin 420b may slide into recess 438, thereby locking anvil 420 in the closed position. In some cases, pin 420b may ride along a wall of recess 438 until pin 420b is engaged within recess 438. A distal movement of elongated member 40 may cause anvil 420 to move distally, releasing second pin 420b from recess 438. A biasing force and/or a force on proximal end 422a may cause anvil to rotate about first pin 420a into the open configuration.

Figure 5A:
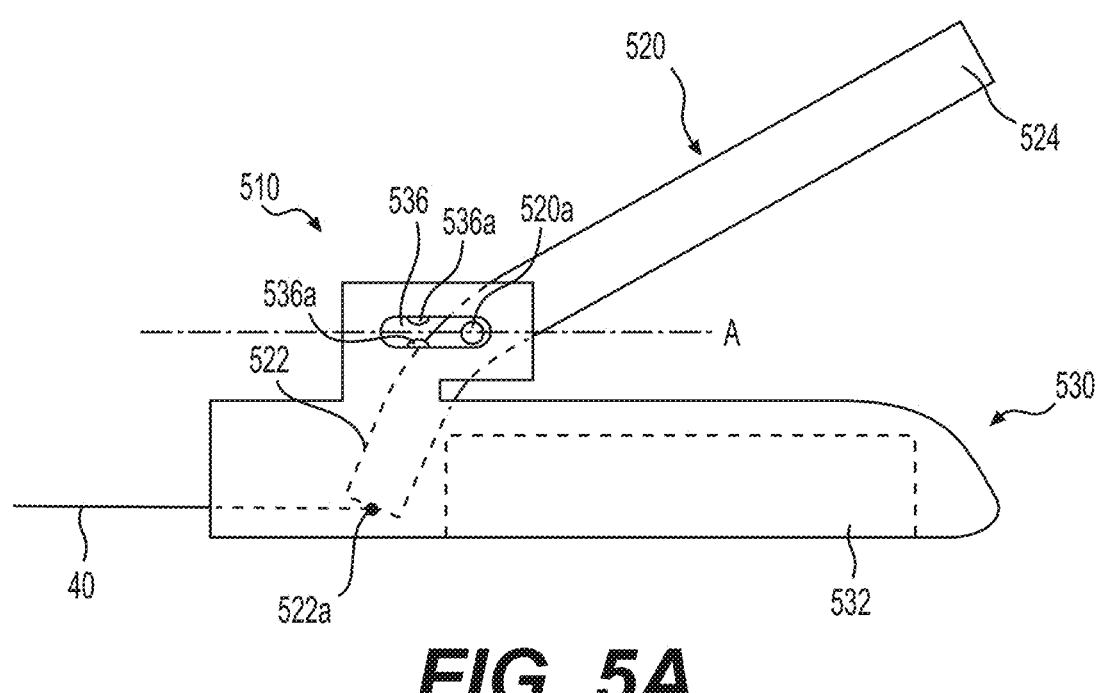
FIGS. 5A and 5B are views of a fastening device of the fastening system of FIG. 1, according to an embodiment.
Figure 5B:
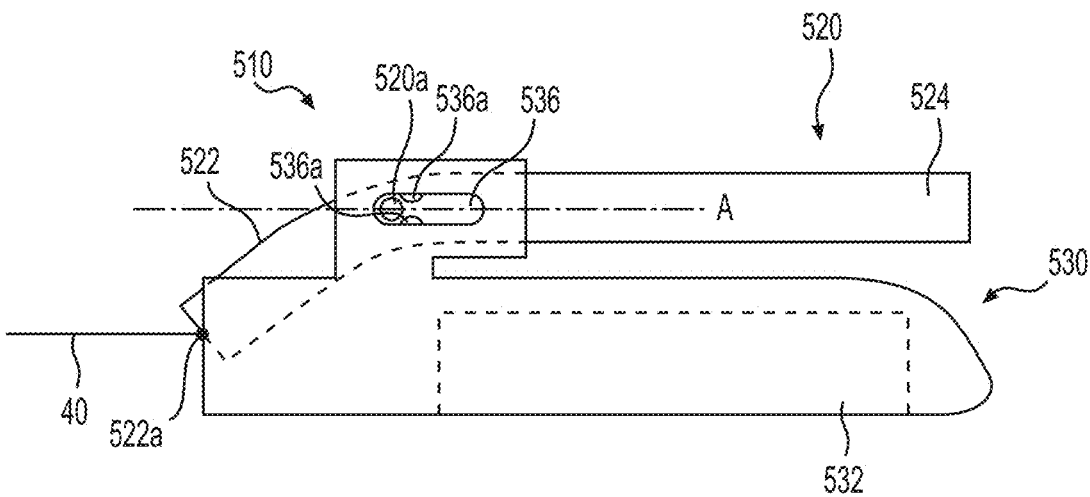

An example of another stapler device 510 having a locking mechanism is shown in FIGS. 5A and 5B. Anvil 520 includes a pin 520a extending from a sidewall of anvil 520, a distal end 524, and a proximal end 522. Pin 520a may move within a slot 536 in a body 530 of stapler device 510. Slot 536 extends from a proximal end of body 530 toward a distal end. A pair of protrusions 536a extend into slot 536 at a proximal end portion thereof. For example, a first protrusion 536a extends from a bottom surface of slot 536 into slot 536, and a second protrusion 536a extends from a top surface of slot 536, opposite the first protrusion 536a, into slot 536. Protrusions 536a may be formed such that they do not move and/or may be made of a material that is able to partially deform as pin 522a passes in the space formed in between the two opposing protrusions 536a. Alternatively, protrusions 536a may include ball-nose spring plungers which may be biased toward a center of slot 536 and may be pushed toward sidewalls of slot 536 when pin 522a is moved past protrusions 536a. A wire 40 is attached to an attachment point 522a at proximal end 522 of anvil 520. A cartridge 532 similar to other cartridges described herein may be disposed within body 530.

An operation of stapler device 510 will now be described. Anvil 520 is in the open position in FIG. 5A, in which distal end 524 is rotated away from body 530. Wire 40 is moved distally, which may cause pin 520a to move proximally within slot 536 and cause anvil 520 to move proximally. Anvil 520 may also rotate about pin 520a, causing distal end 524 to rotate toward body 530 and into the closed position. Pin 520a may move proximally to and past protrusions 536a. For example, protrusions 536a may move toward sidewalls of slot 536 and/or protrusions 536a may be deformed to allow pin 520a to pass. Once pin 520a is positioned proximally of protrusions 536a, anvil 520 is locked in the closed position. To unlock anvil 520, a force is supplied to wire 40 in a distal direction and sufficient to move pin 520a distal to protrusions 536a. Once pin 520a is distal to protrusions 536a, anvil 530 may move distally and may rotate into the open position.

Figure 6A:
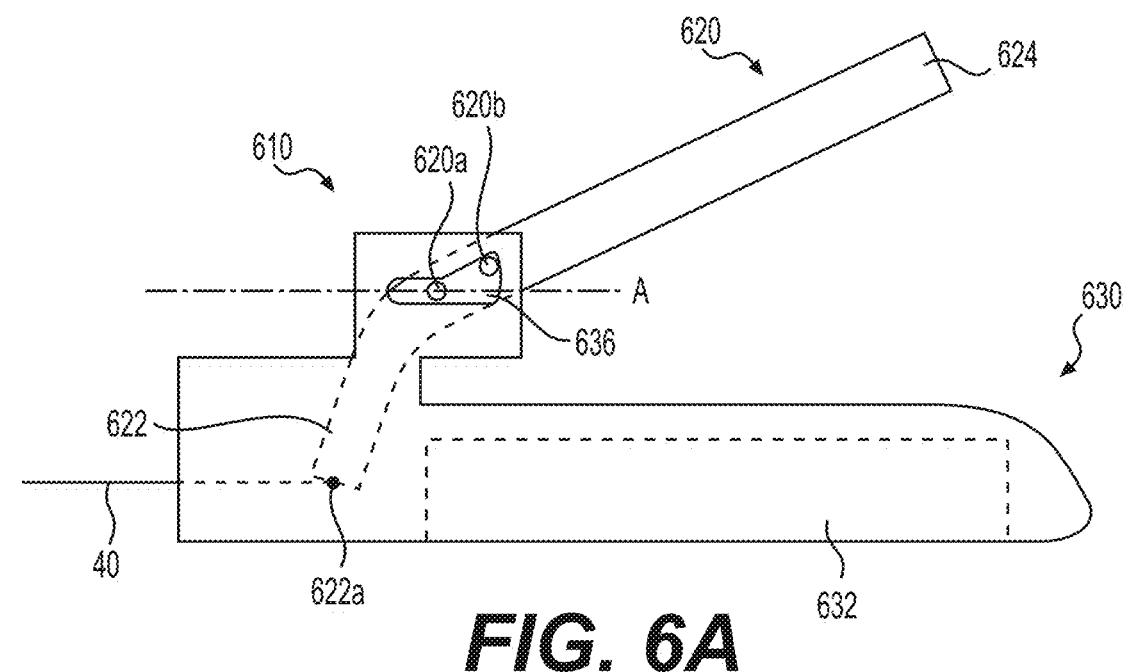
FIGS. 6A and 6B are views of a fastening device of the fastening system of FIG. 1, according to an embodiment.
Figure 6B:
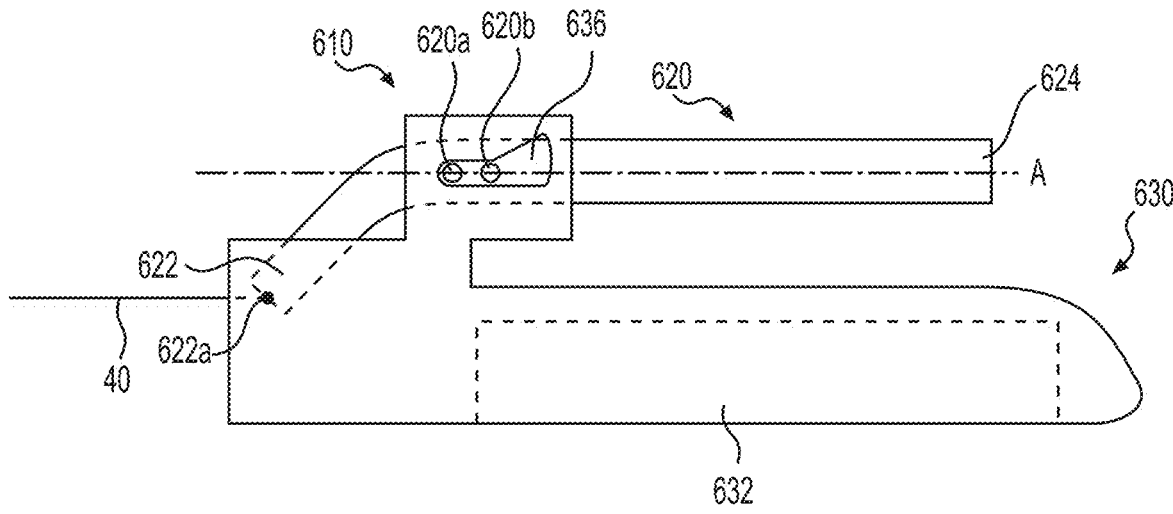

An example of another stapler device 610 having a locking mechanism is shown in FIGS. 6A and 6B. Anvil 610 includes first and second pins 620a, 620b extending from a same side wall of anvil 610, a proximal end 622, and a distal end 624. Pins 620a, 620b may move within a slot 636 in a body 630 of stapler device 610. Slot 636 extends from a proximal end of body 630 toward a distal end and along a longitudinal axis A. Approximately halfway along longitudinal axis A, an upper wall of slot A is angled upward and extends away from the bottom wall of slot 136, increasing the surface area of a distal end of slot 636. An angle between the upper wall of slot A and the bottom wall of slot A may be approximately 30 degrees to approximately 45 degrees. The angled portion of slot 636 enables anvil 620 to move between the open configuration and the closed configuration. A wire 40 is attached to an attachment point 622a at proximal end 622 of anvil 620. A cartridge 632 similar to other cartridges described herein may be disposed within body 630.

A method of operating stapler device 610 now will be described. Wire 40 may be moved in a proximal direction, rotating distal end 624 toward body 630. At a same time, first pin 620a slides proximally along longitudinal axis A, while second pin 620b rides along the angle portion of slot 636. This causes anvil 620 to move toward the closed configuration, i.e., a distal end 624 of anvil 620 approaches body 630 of stapler device 610. FIG. 6B shows both first and second pins 620a, 620b confined to a portion of slot 636 disposed only along longitudinal axis A, which locks anvil 620 in the closed configuration. To unlock the device, wire 40 may be moved distally, which allows second pin 620b to ride up the angled portion of slot 636, opening anvil 620.

Figure 7A:
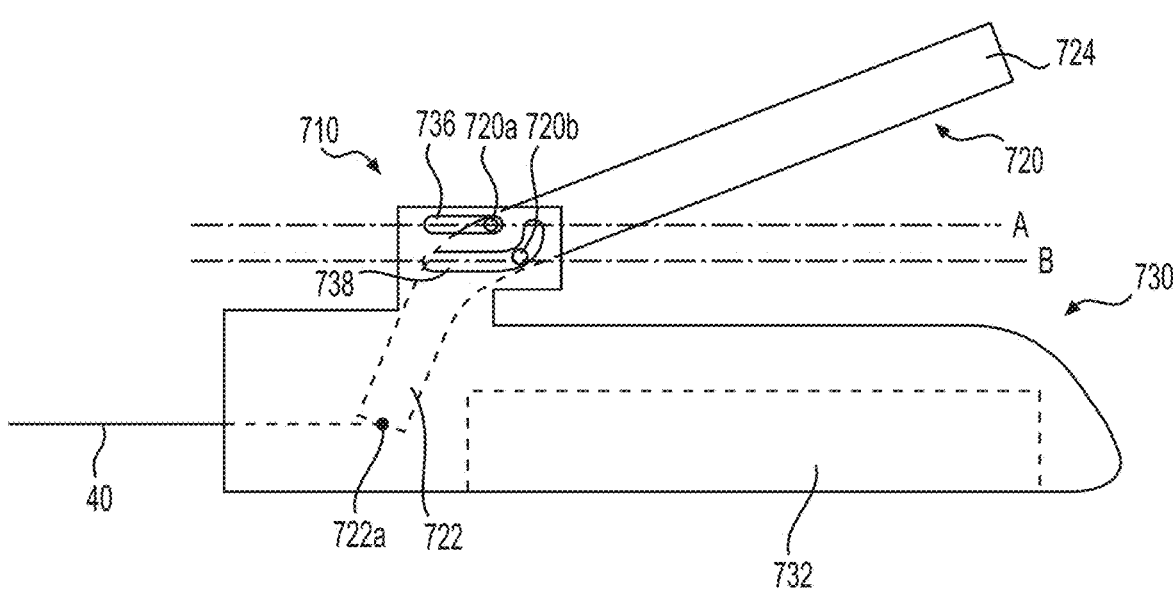
FIGS. 7A and 7B are views of a fastening device of the fastening system of FIG. 1, according to an embodiment.
Figure 7B:
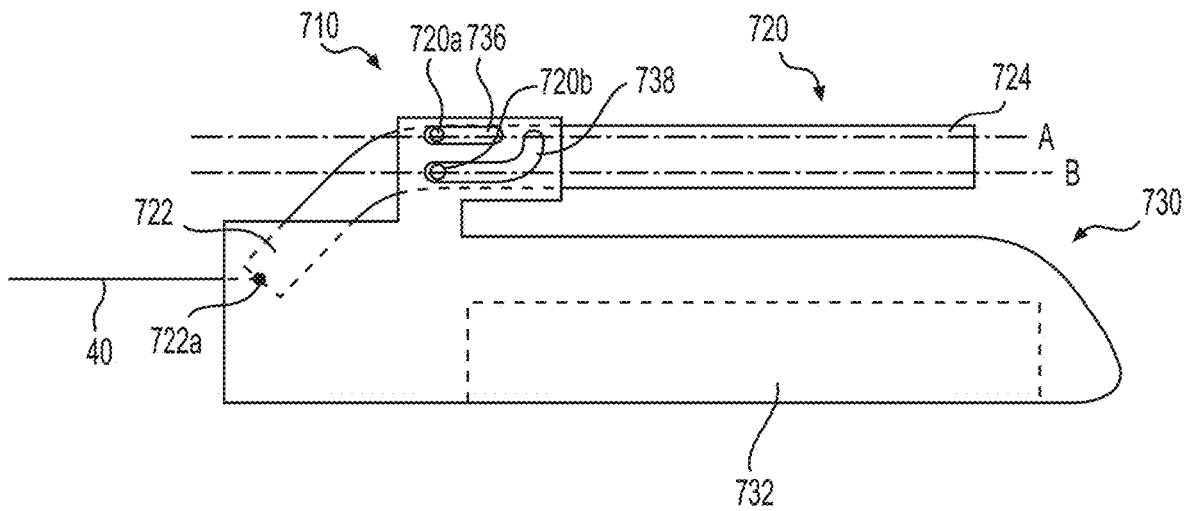

An example of another stapler device 710 is shown in FIGS. 7A and 7B. A body 730 of stapler device 710 includes a first slot 736 extending along a longitudinal axis A and above a second slot 738. A first portion of second slot 738 extends along a longitudinal axis B parallel to longitudinal axis A for a length of first slot 736. Second slot 738 curves upward at a position distal to first slot 736, and second slot 738 terminates approximately at longitudinal axis A. Second slot 738 may terminate above or below longitudinal axis A, depending on a desired angle between anvil 720 and body 730. According to an example, a radius of curvature of the curve of second slot 738 may be equal to a distance between a center of first pin 720a and a center of second pin 720b. An anvil 720 includes a first pin 720a and a second pin 720b extending from a same sidewall of anvil 720 as first pin 720a. First pin 720a extends into first slot 736 and second pin 720b extends into second slot 738. The pin-and-slot arrangement allows anvil 720 to move between the open configuration and the closed configuration. Wire 40 is attached to an attachment mechanism 722*a* on proximal end 722 of anvil 720.

A method of operating stapler device 710 will now be described. Proximal movement of wire 40 causes pin 720*a* to move proximally within first slot 736 and along longitudinal axis A. At the same time, second pin 720*b* travels along the curved portion of second slot 738 and approaches longitudinal axis B, causing a distal end 724 of anvil 720 to approach body 730. When second pin 720*b* reaches longitudinal axis B, pin 720*b* moves proximally within second slot 738 and along longitudinal axis B. Positioning pin 720*b* along longitudinal axis B of second slot 738 locks anvil 720 in the closed configuration. As with other stapler devices described herein, moving wire 40 in a distal direction moves anvil 720 into the open configuration. For example, moving wire 40 in the distal direction pushes anvil 720 distally and causes second pin 720*b* to ride along the curved portion of second slot 730 and into the open position, thereby releasing any tissue grasped between anvil 720 and body 730.

Figures 8A, 8B:
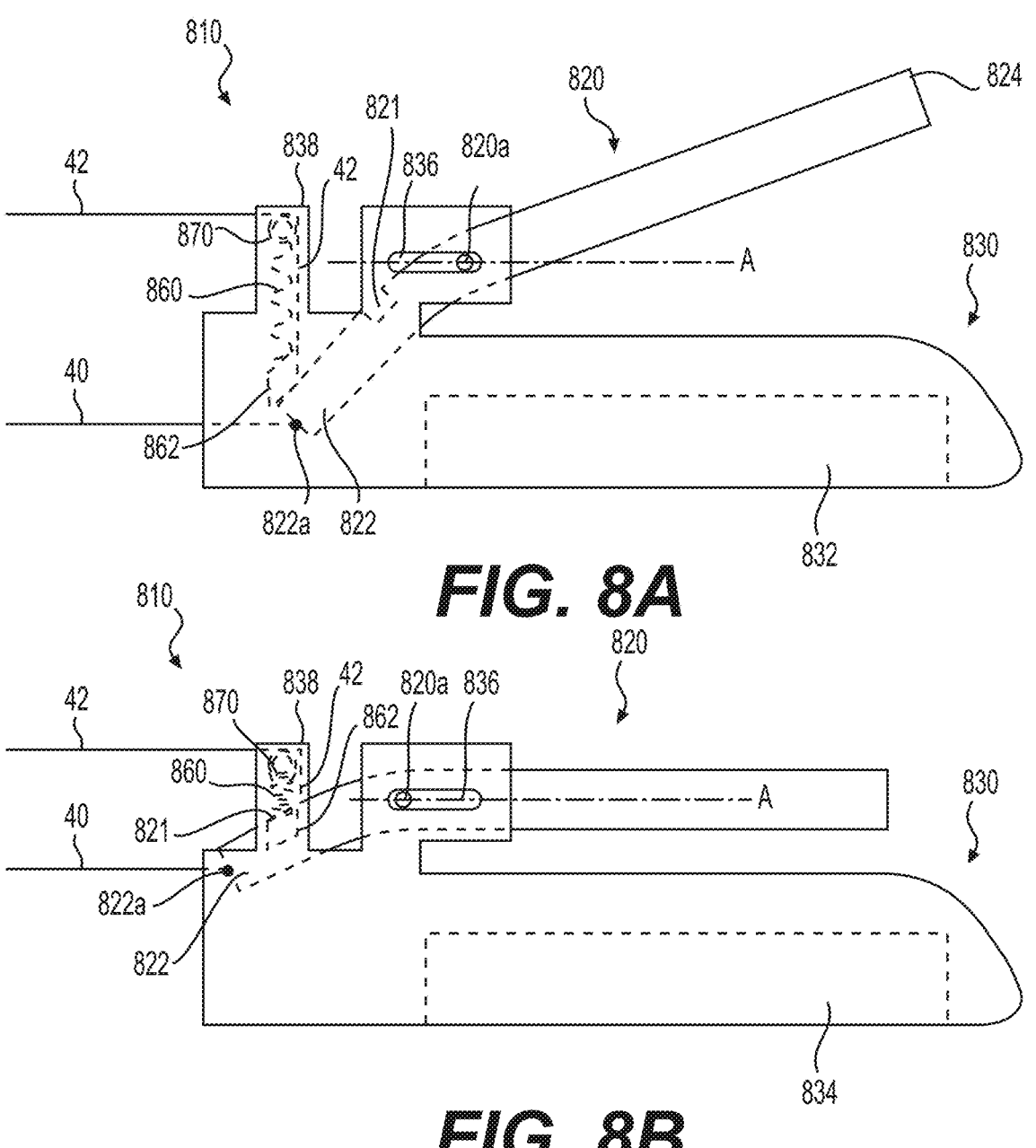
FIGS. 8A and 8B are views of a fastening device of the fastening system of FIG. 1, according to an embodiment.

Another locking mechanism for a stapler device 810 is shown in FIGS. 8A and 8B. Stapler device 810 includes a body 830 having a cartridge 832, a slot 836 extending along a longitudinal axis A. A support member 838 extends approximately perpendicular to and from a top surface of body 830, and the support member 838 is proximal of slot 836. An anvil 820 includes a proximal end 822 and distal end 824, and includes a pin 820*a* extending from a sidewall thereof. Pin 820*a* is configured to slide within slot 836 along longitudinal axis A, and anvil 820 is configured to rotate about pin 820*a*. Wire 40 is attached to an attachment mechanism 822*a* of proximal end 822. A notch 821 extends from a top surface of proximal end 822 into anvil 820.

Support member 838 includes a round member 870, such as a pulley, mounted at an end of support member 838 that is distal of body 810. Round member 870 may rotate about an axis or may be fixed. An actuation wire 42 extends from a proximal end of surgical apparatus 10 and contacts a surface of round member 870. A locking pin 862 may be attached at a distal end of actuation wire 42. Also attached to locking pin 862 is a biasing member 860, such as a spring. Biasing member 860 is attached at a distal end to a same surface of locking pin 862 as actuation wire 42, and is attached at a proximal end to support member 838. Biasing member 860 biases locking pin 862 away from the proximal end of biasing member 860. As shown in FIG. 8B, locking pin 862 is configured to extend into notch 821 to lock anvil 820 is the closed configuration, as will be described herein.

A method of locking stapler device 810 will now be described. FIG. 8A shows anvil 820 in an open configuration in which distal end 824 extends away from body 830. A user may move wire 40 in a proximal direction, causing pin 820*a* (including anvil 820) to slide proximally along longitudinal axis A. Proximal movement of wire 40 also causes anvil 820 to rotate about pin 820*a*, causing distal end 824 to approach body 830. When proximal end 822 of anvil 820 is sufficiently moved in a proximal direction, locking pin 862 is forced into notch 821 via biasing member 860, thereby locking anvil 820 in the closed configuration.

To unlock anvil 820, a force is applied to actuation wire 42, causing actuation wire 42 to ride along the curved surface of round member 870. This causes actuation wire 42 to pull locking pin 862 up and out of notch 821. A force may then be applied to wire 40 in a distal direction, causing pin 820*a* (and anvil 820) to move in the distal direction along longitudinal axis A so as to rotate anvil 820 about pin 820*a*, thereby moving anvil 820 into the open configuration.

Figure 9A:
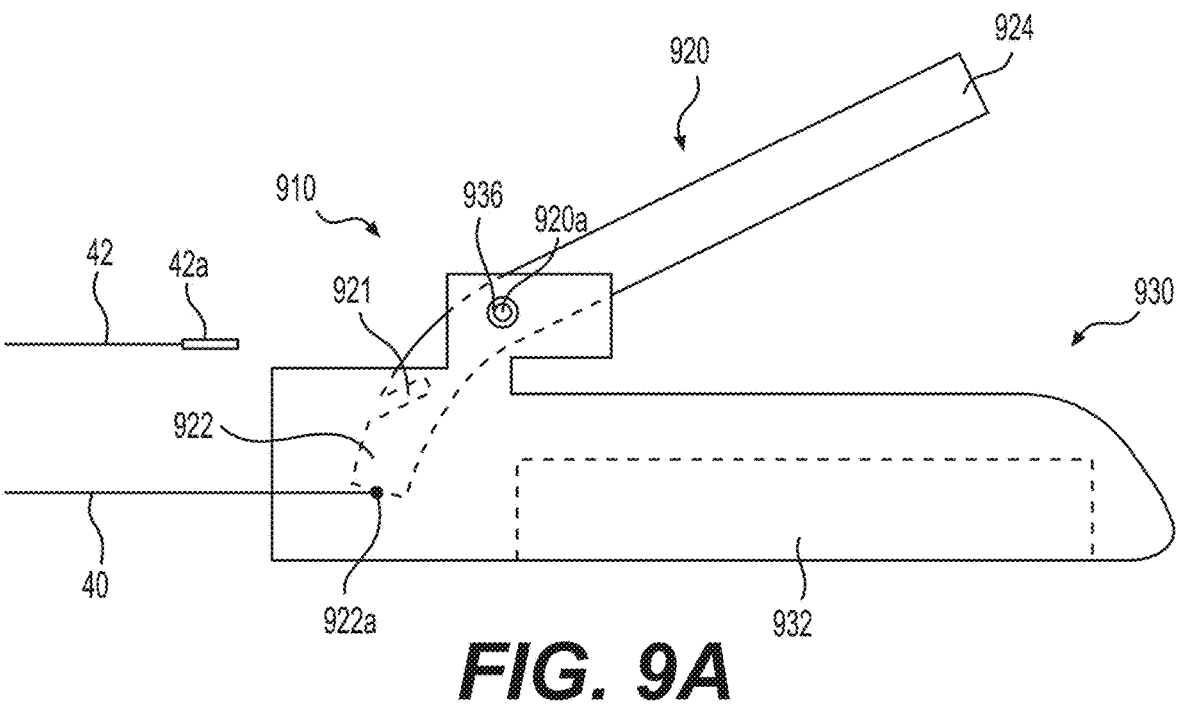
FIGS. 9A and 9B are views of a fastening device of the fastening system of FIG. 1, according to an embodiment.
Figure 9B:
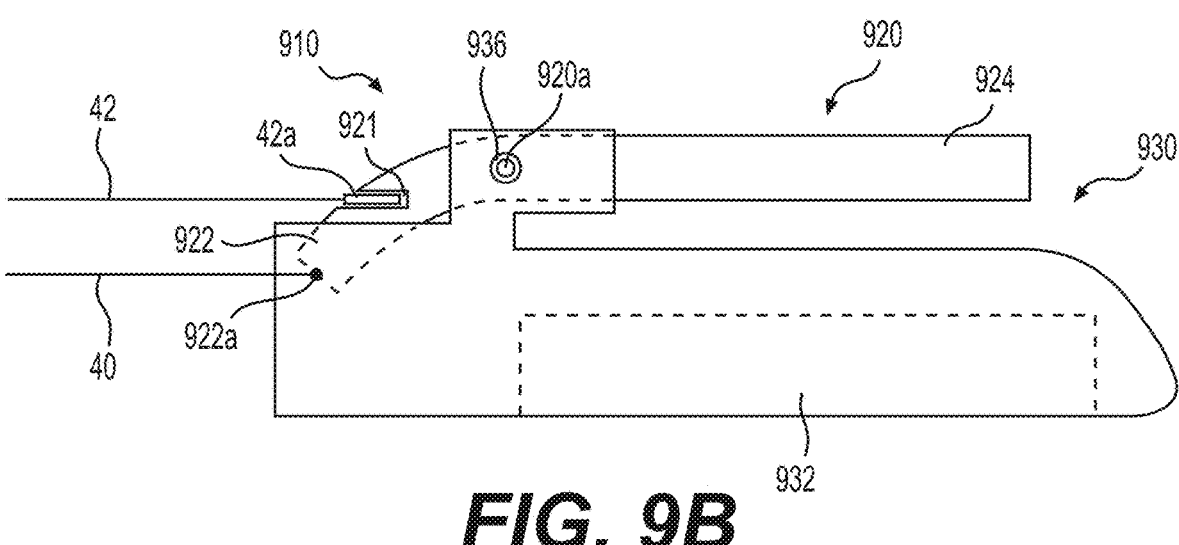

FIGS. 9A and 9B show yet another example of a locking mechanism for a stapler device 910. Stapler device 910 includes a body 930 having a cartridge 932 and a circular opening 936. A pin 920*a* extending from an anvil 924 may be received within opening 936, and anvil 920 may rotate about pin 920*a*, moving a proximal end 922 and a distal end 924 of anvil 920 from the open configuration to the closed configuration. While stapler device 910 is shown with circular opening 936, stapler device 910 may alternatively include a slot (such as a slot described in examples herein), which may allow anvil 920 to move proximally and/or distally within the slot in addition to rotating about pin 920*a*. Wire 40 is attached to an attachment mechanism 922*a* at proximal end 922. Proximal end 922 also includes a notch 921, which faces a proximal direction when anvil 920 is in the closed configuration (FIG. 9B). Notch 921 may receive a locking pin 42*a* attached to a distal end of actuation wire 42 to lock anvil 920 in the closed configuration. A user may move actuation wire 42 proximally and distally. Alternatively, or additionally, actuation wire 42 may be biased in the distal direction via a biasing member (e.g., a spring). Proximal movement of actuation wire 42 may overcome the biasing mechanism to withdraw locking pin 42*a* from notch 921.

An operation of stapler device 910 will now be described. In the open configuration shown in FIG. 9A, distal end 924 of anvil 920 is rotated away from body 930. Proximal movement of wire 40 causes anvil 920 to rotate about pin 920*a*, moving distal end 924 toward body 930 and into the closed configuration. Rotation of anvil 920 also allows proximal end 922 to move upward and proximally, aligning notch 921 with locking pin 42*a*. Once notch 921 and locking pin 42*a* are aligned, actuation wire 42 may be moved distally, causing locking pin 42*a* to engage notch 921 and locking anvil 920 in the closed configuration, as shown in FIG. 9B. The position of locking pin 42*a* may be maintained through friction forces. Alternatively, while locking pin 42*a* is positioned in notch 921, actuation wire 42 may be moved at a same time and in a same direction as stapler device 910, maintaining a position of locking pin 42*a* in notch 921. To unlock stapler device 910, the user may move actuation wire 42 proximally, causing locking pin 42*a* to be moved out of notch 921. The user may subsequently move wire 40 in the distal direction, rotating anvil 920 about pin 920*a* to move anvil 920 into the open configuration.

Figure 10A:
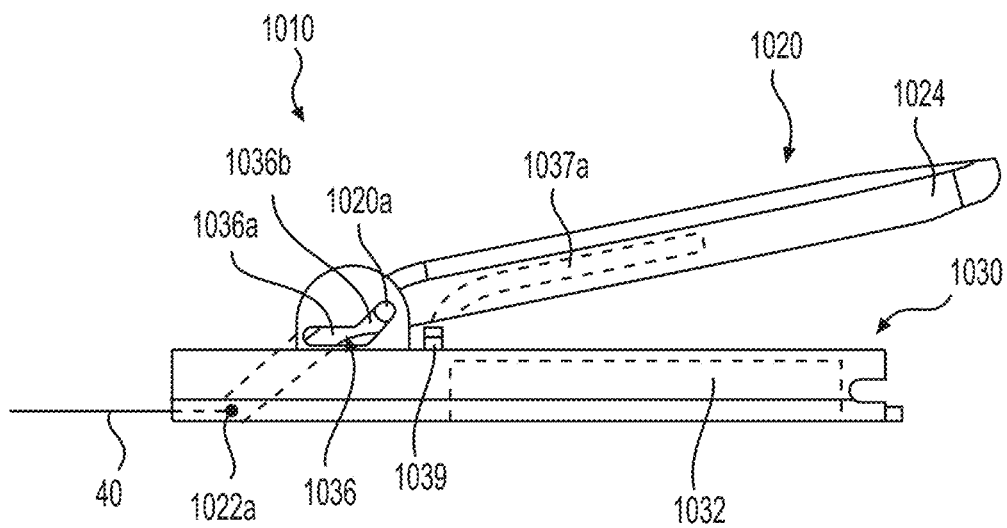
FIGS. 10A-10C are views of a fastening device of the fastening system of FIG. 1, according to an embodiment.
Figure 10B:
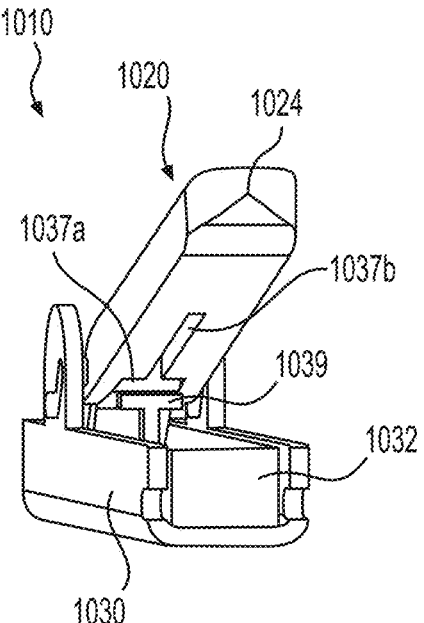
Figure 10C:
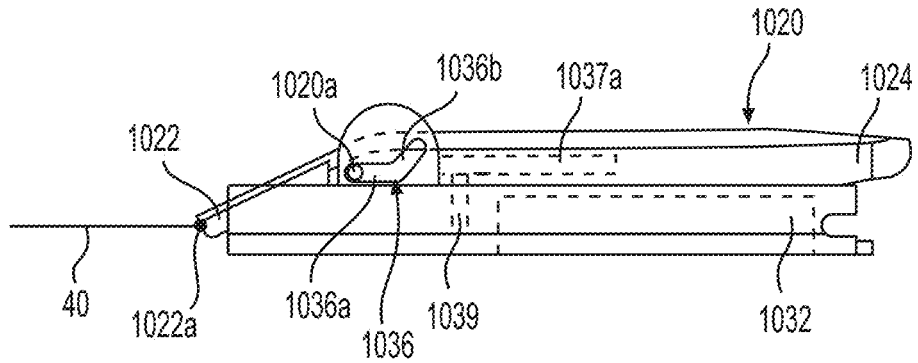

Another example of a locking mechanism for a stapler device 1010 is shown in FIGS. 10A-10C. Stapler device 1010 includes a body 1030 having a slot 1036, and an anvil 1020 having a pin 1020*a* slidable within slot 1036. Slot 1036 includes a first arm 1036*a* extending longitudinally, and a second arm 1036*b* extending from a distal end of first arm 1036*a*. An angle formed between first arm 1036*a* and second arm 1036*b* is between approximately 90 degrees and 180 degrees, or approximately 135 degrees. Similar to other stapler devices described herein, wire 40 extends from an attachment mechanism 1022*a* of anvil 1020. Proximal and distal movement of wire 40 may cause pin 1020*a* to slide within slot 1036 to cause anvil 1020 to move proximally and distally.

A T-shaped member 1039 protrudes perpendicularly from a bottom of body 1030 toward anvil 1020. T-shaped member 1039 may be proximal of a cartridge 1032 disposed in body 1030, or T-shaped member 1039 may protrude through cartridge 1032. Anvil 1020 includes a perpendicular slot 1037*a* connected to a longitudinal slot 1037*b*. Perpendicular slot 1037*a* is positioned proximal to longitudinal slot 1037*b*, and longitudinal slot 1037*b* extends distally from perpendicular slot 1037*a*. As shown in FIGS. 10A and 10C, perpendicular slot 1037*a* extends inside anvil 1020 along a length of longitudinal slot 1037*b*. For example, longitudinal slot 1037*b* and perpendicular slot 1037*a* form a T-shaped slot to receive T-shaped member 1039. A top portion of T-shaped member 1039 is configured to engage with perpendicular slot 1037*a*. After T-shaped member 1039 is engaged with perpendicular slot 1037*a*, proximal movement of anvil 1020 may cause perpendicular slot 1037*a* to move proximally of T-shaped member 1039, causing the leg of T-shaped member 1039 to protrude through and slide along longitudinal slot 1037*b*. In this manner, anvil 1020 may be locked against T-shaped member 1039.

An operation of anvil 1020 includes moving anvil 1020 into the open configuration in a manner similar to those described herein. For example, a force applied to wire 40 may move anvil 1020 in a proximal direction. When pin 1020*a* moves along the second arm 1036*b* of slot 1036, anvil 1020 is pushed upward and T-shaped member 1039 disengages perpendicular slot 1037*a*, thereby moving anvil 1020 to the open configuration.

Figures 11A, 11B:
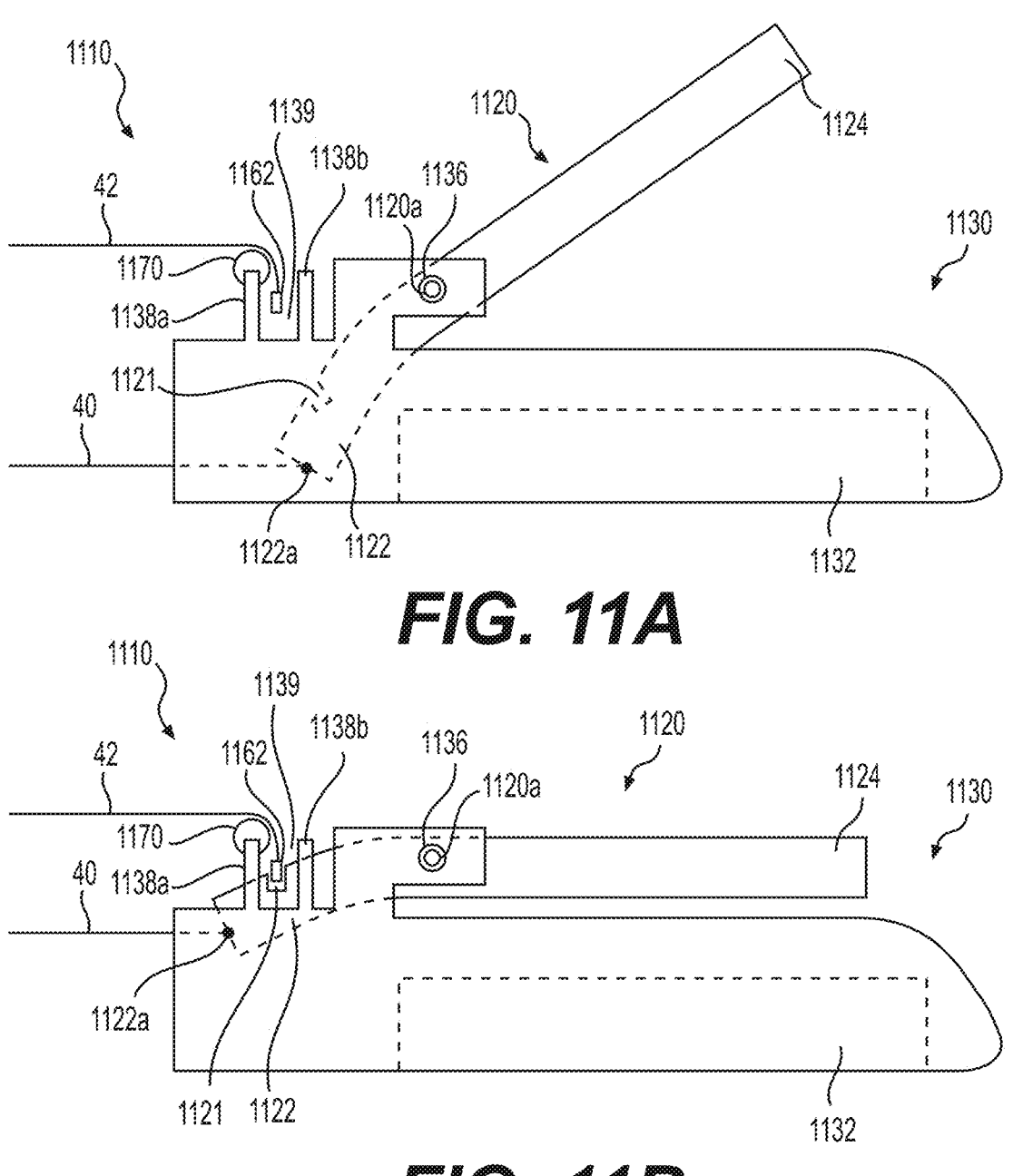
FIGS. 11A and 11B are views of a fastening device of the fastening system of FIG. 1, according to an embodiment.

Yet another locking mechanism for a stapler device 1110 is shown in FIGS. 11A and 11B. Stapler device 1110 is similar to stapler device 1010, including a body 1130 having a cartridge 1132, a circular opening 1136, and two support members 1138*a*, 1138*b* extending from a top surface of body 1130 proximal of opening 1136. An anvil 1120 includes a proximal end 1122 and a distal end 1124, and includes a pin 1120*a* extending from a sidewall of anvil 1120. Anvil 1120 is configured to rotate about pin 1120*a*. Wire 40 is attached to an attachment mechanism 1122*a* of proximal end 1122. While stapler device 1110 is shown with circular opening 1136, stapler device 1110 may alternatively include a slot (such as a slot described in various examples herein), which may allow anvil 1120 to move proximally and/or distally in addition to rotating about pin 1120*a*. A notch 1121 extends from a top surface of proximal end 1122 into anvil 1120.

Proximal support member 1138*a* includes a round member 1170, such as a pulley. Round member 1170 is mounted at an end distal of body 1130. Round member 1170 may rotate about an axis or may be fixed. An actuation wire 42 extends from a proximal end of surgical apparatus 10 and contacts a surface of round member 1170. A locking pin 1162 may be attached at a distal end of actuation wire 42. Locking pin 1162 may extend into and move along a channel 1139 defined between support members 1138*a*, 1138*b*. As shown in FIG. 11B, locking pin 1162 is configured to extend into notch 1121 to lock anvil 1120 in a closed configuration, as will be described herein.

A method of locking stapler device 1110 will now be described. FIG. 11A shows anvil 1120 in an open configuration, as described herein. A user may move wire 40 in a proximal direction, causing anvil 1120 to rotate about pin 1120*a*, which in turn causes distal end 1124 to approach body 1130 and causes proximal end 1122 to move upward, aligning slot 1121 with channel 1139. The user may subsequently move actuation wire 42 in the distal direction, engaging locking pin 1120*a* with slot 1121, thereby locking anvil 1120 in the closed position.

To unlock anvil 1120, a proximal force is applied to actuation wire 42, causing actuation wire 42 to ride along the curved surface of round member 1170 and move locking pin 1162 within channel 1139 and out of slot 1121. A distal force may then be applied to wire 40, causing anvil 1120 about pin 1120*a*, thereby moving anvil 1120 into the open configuration.

Alternatively, locking pin 1162 may be introduced from a bottom of a body 1130. For example, channel 1139 may extend from a bottom surface of and into body 1130. In other words, rounded surface 1170 and support members 1138*a*, 1138*b* may extend from a bottom surface of body 1130. Operation of actuation wire 42 and locking pin 1162 is the same as the configuration in which support members 1138*a*, 1138*b* extend from a top surface of body 1130.

Figures 12A, 12B, 12C:
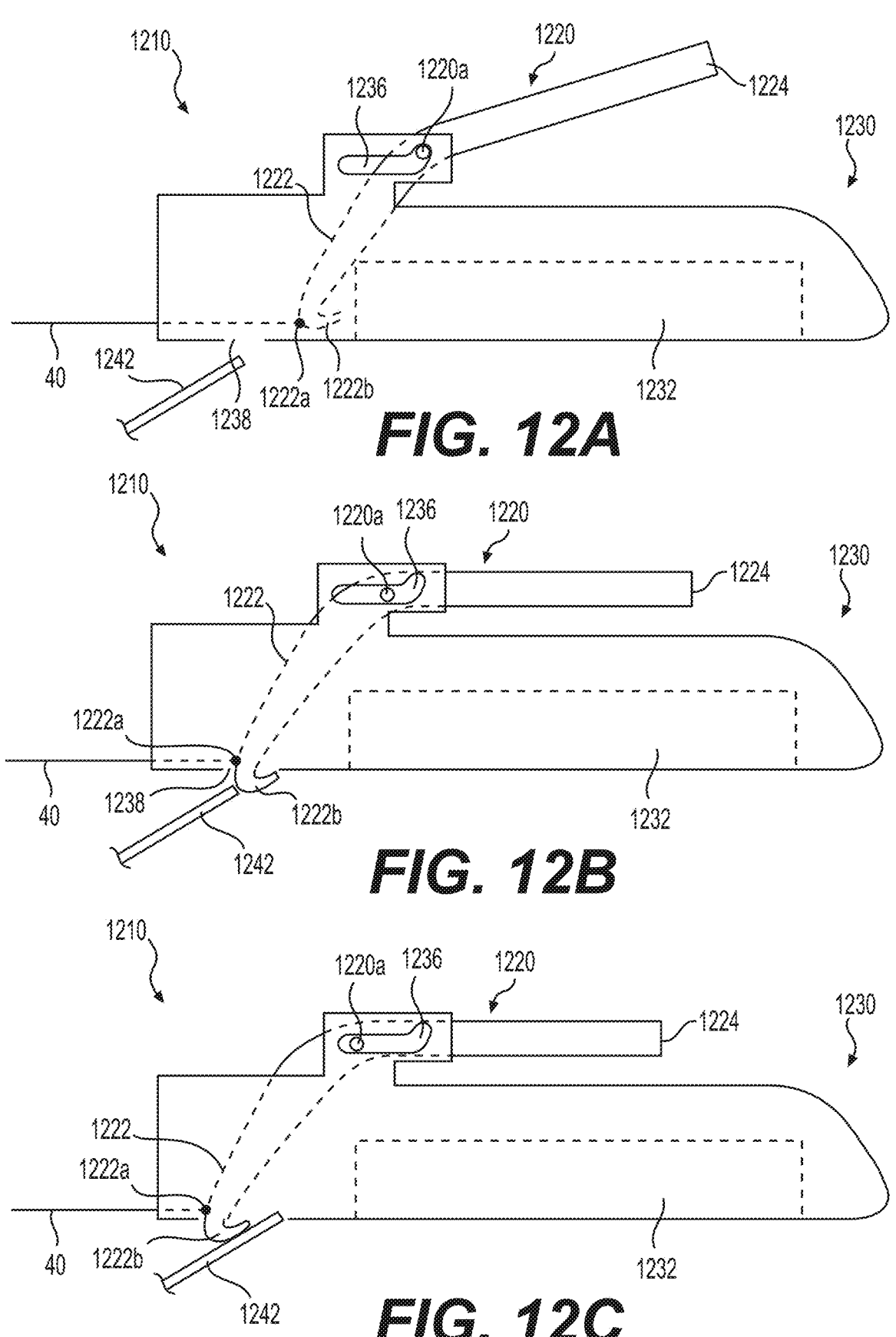
FIGS. 12A-12C are views of a fastening device of the fastening system of FIG. 1, according to an embodiment.

An example of another stapler device 1210 having a locking mechanism is shown in FIGS. 12A-12C. Anvil 1220 includes a pin 1220*a* extending from a sidewall of anvil 1210, a distal end 1224, and a proximal end 1222. Pin 1220*a* may move within a slot 1236 in a body 1230 of stapler device 1210. Slot 1236 extends from a proximal end of body 1230 toward a distal end, and may include a second portion angled upwards. It will be understood that this additional portion may provide additional range of motion for anvil 1230. Proximal end 1222 includes a distally facing hook 1222*b* and may mate with an opening 1238 in a bottom surface of body 1230. A release mechanism 1242 may extend from below body 1230 toward a bottom surface of body 1230. Release mechanism 1242 may be a flat element that acts as a ramp, as shown in FIG. 12C. A wire 40 is attached to an attachment point 1222*a* at proximal end 1222 of anvil 1220. A cartridge 1232 similar to other cartridges described herein may be disposed within body 1230.

An operation of stapler device 1210 will now be described. Anvil 1220 is in the open position in FIG. 12A, in which distal end 1224 is rotated away from body 1230. Wire 40 is moved distally, which may cause pin 1220*a* to move proximally within slot 1236 and cause anvil 1220 to move proximally. Anvil 1220 may also rotate about pin 1220*a*, causing distal end 1224 to rotate toward body 1230 and into the closed position. As anvil 1230 moves proximally, hook 1222*b* may engage opening 1238 and a bottom surface of body 1230, thereby locking anvil 1230 in the closed position, as shown in FIG. 12B. To unlock anvil 1230, wire 40 is moved proximally, causing hook 1238 to disengage from the bottom surface of body 1230. Release mechanism 1242 may subsequently be moved into opening 1238 distal to hook 1222*b*, as shown in FIG. 12C. Wire 40 may then be moved in a distal direction, moving anvil 1220 distally and sliding hook 1222*b* along a top surface of release mechanism 1242. This may allow hook 1222*b* to move distal to opening 1238 without engaging opening 1238, thereby unlocking anvil 1220. Once hook 1222*b* is distal to opening 1238, anvil 1220 may move distally and may rotate into the open position.

Figure 13A:
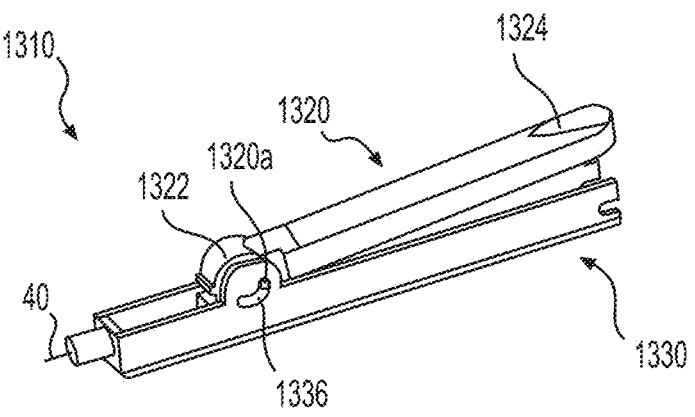
FIGS. 13A-13C are views of a fastening device of the fastening system of FIG. 1, according to an embodiment.
Figure 13B:
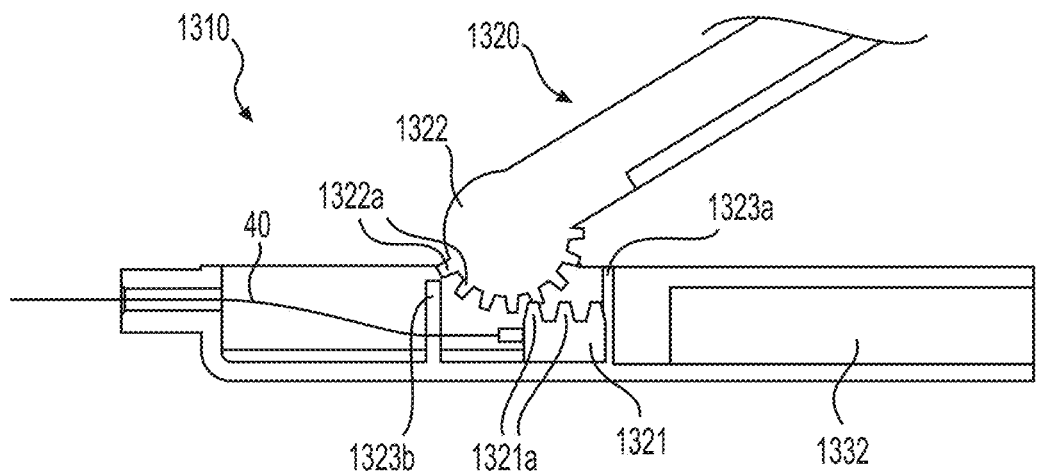
Figure 13C:
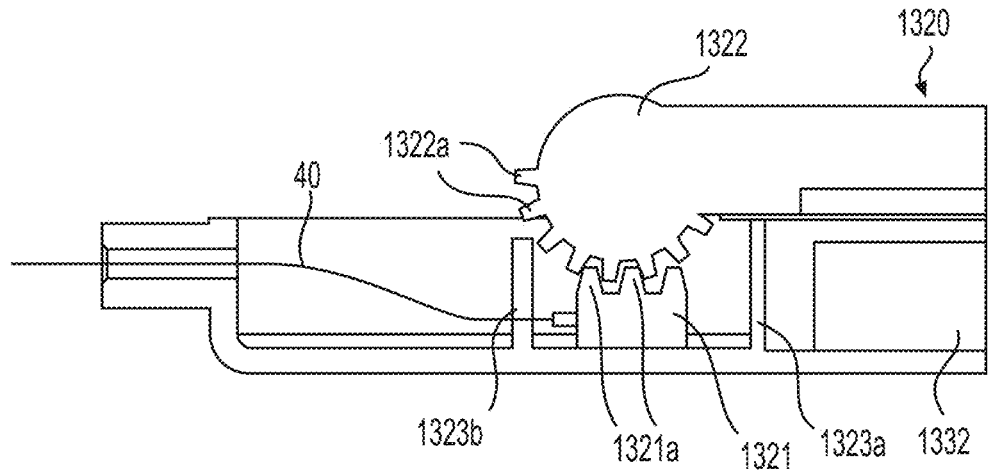

An example of another locking mechanism for a stapler device is shown in FIGS. 13A-13C. Stapler device 1310 of surgical apparatus 10 is similar to other stapler devices described herein, and includes a body 1330 with a cartridge 1332 and an anvil 1320 pivotally connected thereto. A pin 1320*a* extends from a side of anvil 1320 and slides within a slot 1336 of body 1330. Slot 1336 may be curved, as shown in FIG. 13A, but is not limited to this configuration. Wire 40 extends from a proximal end of a gear slider 1321 (see FIG. 13B), and wire 40 is configured to extend from a proximal end of body 1330 and move proximally and distally.

As shown in FIG. 13B, a plurality of teeth 1322*a* extend circumferentially from a circular proximal end 1322 of anvil 1320. Teeth 1322*a* may contact and cooperate with a gear slider 1321 and corresponding teeth 1321*a* extending from a surface of gear slider 1321. Wire 40 extends from the proximal end of gear slider 1321, and movement of wire 40 may allow gear slider 1321 to move proximally and distally. For example, teeth 1321*a* of gear slider 1321 and teeth 1322*a* of proximal end 1322 form a rack-and-pinion configuration to move anvil 1320.

To operate stapler device 1310, a user may move wire 40 proximally and distally. Distal movement of wire 40 causes anvil 1320 to move into the open configuration. Proximal movement of wire 40 causes anvil 1320 to move into the closed configuration. Anvil 1320 may be locked in the open or closed configuration via friction forces between teeth 1322*a* on anvil 1320 and teeth 1321*a* on gear slider 1321.

Figure 14A:
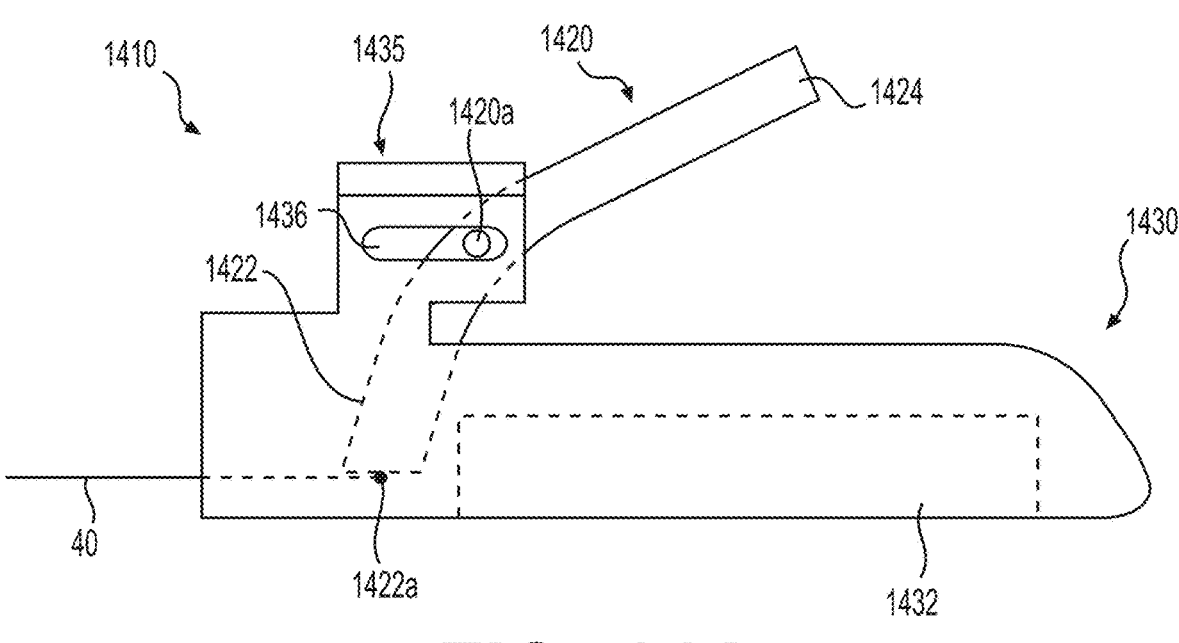
FIGS. 14A and 14B are views of a fastening device of the fastening system of FIG. 1, according to an embodiment.
Figure 14B:
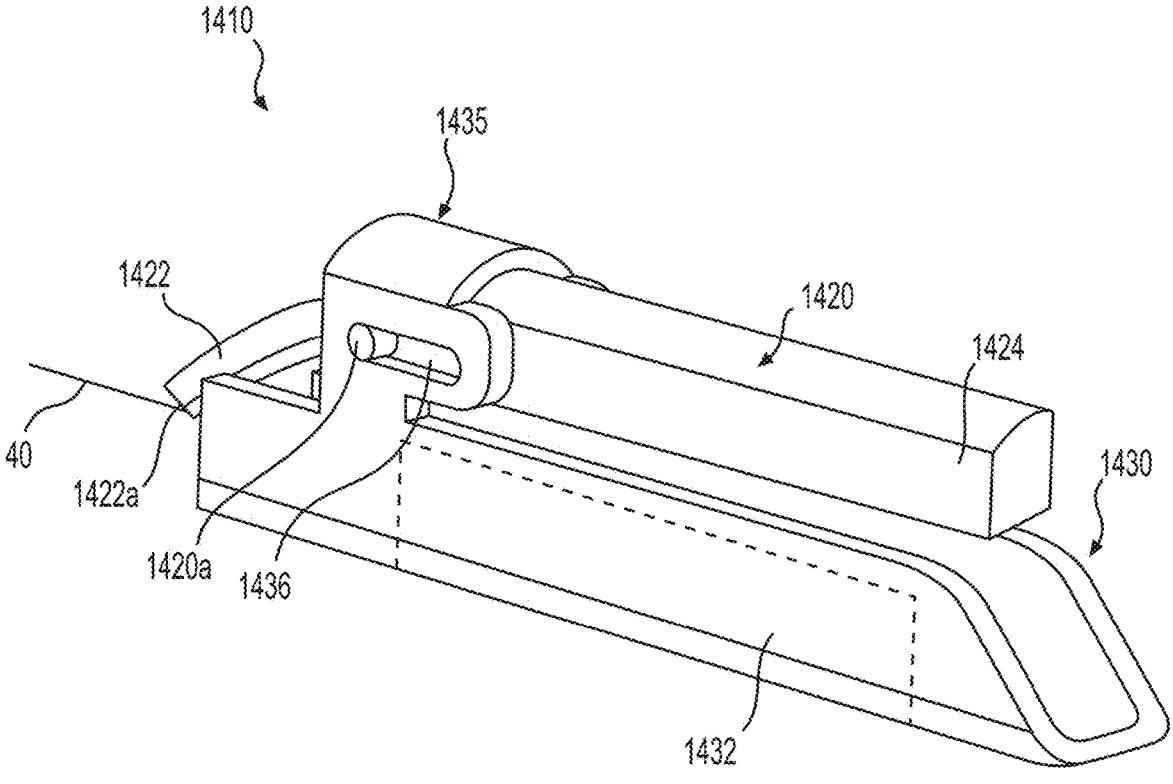

Another stapler device 1410 is shown in FIGS. 14A and 14B. Stapler device 1410 includes a body 1430, a cartridge 1432, and a hood 1435. Body 1430 may include an extension portion extending up from body 1430 and shaped to receive hood 1435. Hood 1435 may be attached to body 1430 by any mechanism including welding, adhesive, or the like. Alternatively, hood 1435 may be formed as a single part with body 1430. Hood 1435 includes a slot 1436 extending in a proximal-distal direction along a longitudinal axis A. In some configurations, e.g., where hood 1435 is not integrally formed with body 1430, slot 1436 is not disposed on body 1430 until hood 1435 is attached to body 1430. An anvil 1420 includes a proximal end 1422, a distal end 1424, a pin 1420*a* extending from a side of anvil 1420, and an attachment point 1422*a* at proximal end 1422. Wire 40 is attached to attachment point 1422*a*. Anvil 1420 is configured to rotate about pin 1420*a*, and pin 1420*a* and anvil 1420 may move along longitudinal axis A. Hood 1435 includes a top portion 1437 that connects sidewalls 1439 and defines a channel 1438 (see FIG. 14C). As will be described herein, channel 1438 may receive anvil 1420 and top portion 1437 may contact anvil 1420 and force anvil 1420 into the closed position.

A method of operating stapler device 1410 will now be described. Anvil 1420 is in the open configuration in FIG. 14A when pin 1420*a* is disposed at a distal end of slot 1436. Movement of wire 40 in the proximal direction causes proximal end 1422 to move upwards and proximally. Anvil 1420 contacts an inside surface of top portion 1437 of hood 1435, forcing distal end 1424 toward body 1430 and into the closed position. Continued proximal movement of wire 40 moves pin 1420*a* along longitudinal axis A to the proximal end and causes anvil 1420 to rotate completely toward body 1430. Top portion 1437 of hood 1435 contacts anvil 1420 in the closed position and assists in locking anvil 1420 in the closed position.

To open anvil 1420, wire 40 is moved distally, causing pin 1420*a* to slide distally within slot 1436 along longitudinal axis A. As anvil 1420 slides distally of hood 1435, anvil 1420 may rotate about pin 1420*a* such that distal end 1424 rotates upward and away from body 1430 into the open configuration.

Figure 14C:
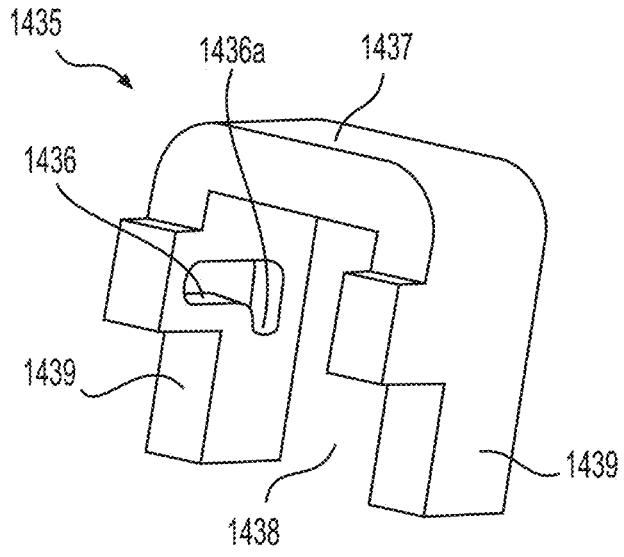
FIGS. 14C-14F are views of a fastening device of a locking mechanism and an attachment position of the locking mechanism of the fastening device of FIGS. 14A and 14B.
Figure 14D:
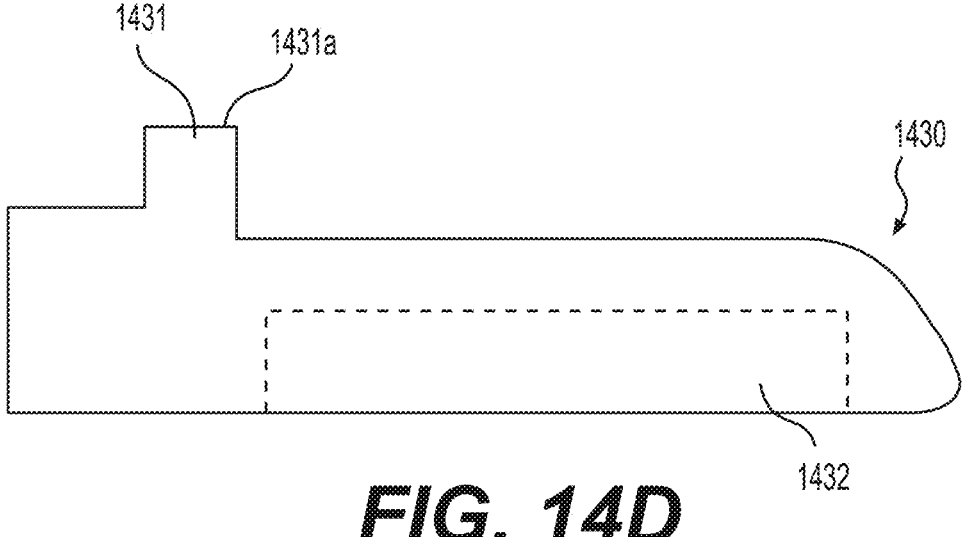

FIGS. 14C-14F show various hood designs and attachment points of the hoods to the body of stapler device 1430. For example, as discussed herein, FIG. 14C illustrates hood 1435 according to an example. Hood 1435 includes top portion 1437 connecting sidewalls 1439, which define channel 1438. When hood 1435 is connected to body 1430 (see FIG. 14D), slot 1436 extends in a proximal-distal direction. A perpendicular slot 1436*a* extends perpendicularly downward from a distal end of slot 1436. Perpendicular slot 1436*a* may receive pin 1420*a* during assembly. The open end of perpendicular slot 1436*a* may be closed when hood is attached to a wall 1431 of body 1430. For example, sidewalls 1438 may be disposed on an outer surface of walls 1431. Hood 1435 may be positioned and attached such that a top surface 1431*a* of each of walls 1431 covers perpendicular slot 1436*a*, thereby securing pin 1420*a* within slot 1436.

Figure 14E:
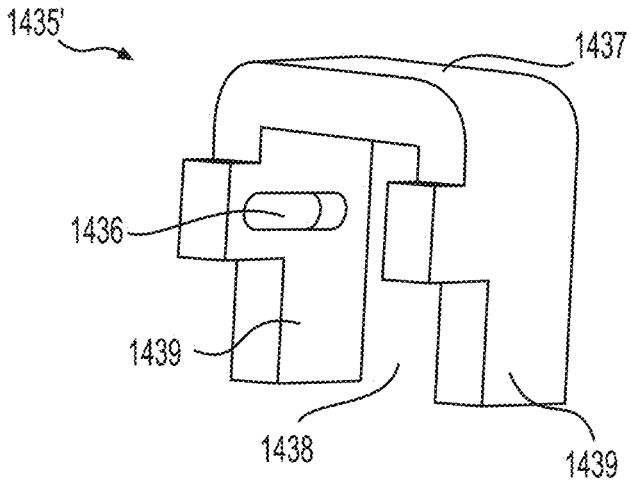

Another hood 1435' is shown in FIG. 14E. Hood 1435' does not include perpendicular slot 1436*a*. Pin 1420*a* may engage slot 1436 by forcing sidewalls apart during assembly. Hood 1435' may be attached to walls 1431 using any method described herein.

Figure 14F:
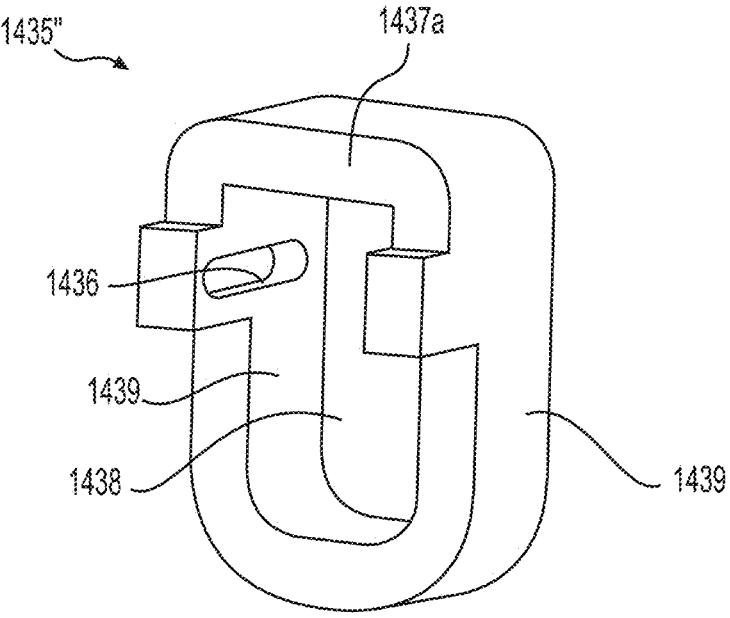

FIG. 14F shows a hood 1435" according to yet another example. Sidewalls 1439 of hood 1435" are connected by both a top portion 1437*a* and a bottom portion 1437*b*. Hood 1435" may slide over body 1430 during assembly and may be attached to sidewalls 1431 using any method described herein.

It will be understood that any of the locking mechanisms described herein may be used along or in combination with one or more other locking mechanisms described herein.

While different medical systems have been described, it will be understood that the particular arrangements of elements in these fastening systems are not limited. Moreover, a size, a shape, and/or the materials of the fastening system are not limited. As described herein, various locking mechanisms for maintaining a closed configuration of the anvil during a fastening procedure. For example, in certain procedures, performing various medical procedures may be improved by ensuring proper fastening of tissues.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A tissue fastening device comprising:
 a body including a ramp and a sidewall, wherein the sidewall includes a slot that extends along a longitudinal axis of the body;
 an anvil pivotally coupled to the body, wherein the anvil is configured to move between an open position and a closed position, and wherein the anvil includes a pin; and
 a wire coupled to a proximal end of the anvil;
 wherein the ramp includes (i) a sloped surface on a distal end of the ramp and (ii) a top surface parallel to a bottom surface of the body, wherein the body and the anvil are configured such that movement of the wire in a proximal direction causes the anvil to slide along the sloped surface of the ramp and the pin to slide proximally along the slot of the body, so that the proximal end of the anvil moves onto the top surface of the ramp, thereby locking the anvil in a closed position.

2. The tissue fastening device of claim 1, wherein the anvil is substantially parallel to the body when the anvil is locked in the closed position.

3. The tissue fastening device of claim 1, wherein the ramp comprises two parallel ramp bodies defining a channel between the ramp bodies.

4. The tissue fastening device of claim 3, wherein the wire extends through the channel.

5. The tissue fastening device of claim 1, wherein a distal end of the ramp is rounded.

6. The tissue fastening device of claim 1, wherein the pin is at a proximal end of the anvil, and wherein the slot is at a proximal end of the body that is proximal of a fastener cartridge of the body.

7. The tissue fastening device of claim 1, wherein the wire is a single wire, wherein proximal movement of only the single wire moves the pin proximally along the slot.

8. A tissue fastening device comprising:

a body including a ramp and a sidewall, wherein the sidewall includes a slot that extends along a longitudinal axis of the body;

an anvil pivotably coupled to the body at a pivot, wherein the anvil includes a pin; and a wire coupled to a proximal end of the anvil, wherein the body and the anvil are configured such that proximal movement of the wire moves the proximal end of the anvil proximally along a sloped surface of the ramp and onto a top surface of the ramp in order to transition the anvil from an open position to a closed position and to lock the anvil in the closed position, and wherein the body and the anvil are configured such that the proximal movement of the wire moves the pin proximally through the slot.

9. The tissue fastening device of claim 8, wherein the ramp comprises two parallel ramp bodies defining a channel between the ramp bodies.

10. The tissue fastening device of claim 9, wherein the wire extends through the channel.

11. The tissue fastening device of claim 8, wherein the pin is at a proximal end of the anvil, and wherein the slot is at a proximal end of the body that is proximal of a fastener cartridge of the body.

12. A tissue fastening device comprising:

a body including:

a ramp, wherein the ramp includes two ramp bodies defining a channel between the ramp bodies; and a sidewall, wherein the sidewall includes a slot that extends along a longitudinal axis of the body;

an anvil including a pin, wherein the anvil is pivotally coupled to the body by the pin engaging the slot and sliding relative to the body within the slot, wherein the anvil is configured to move from an open position to a closed position as the pin slides proximally through the slot; and a wire coupled to a proximal end of the anvil, wherein the wire extends through the channel in the open position of the anvil, wherein the proximal end of the anvil is distal to the ramp in an open position of the anvil, wherein proximal movement of the wire causes the proximal end of the anvil to move proximally, up a sloped surface of the ramp and onto a top surface of the ramp, thereby closing the anvil.

13. The tissue fastening device of claim 12, wherein proximal movement of the wire is configured to rotate the anvil about the pin and slide the pin proximally through the slot.

14. The tissue fastening device of claim 12, wherein the pin is at a proximal end of the anvil, and wherein the slot is at a proximal end of the body that is proximal of a fastener cartridge of the body.

* * * * *